(12) United States Patent
Balwani et al.

(10) Patent No.: US 8,895,061 B2
(45) Date of Patent: Nov. 25, 2014

(54) COMPOSITIONS COMPRISING CARISOPRODOL AND METHODS OF USE THEREOF

(75) Inventors: Gul Balwani, Princeton Junction, NJ (US); Harry J. Sacks, New Brunswick, NJ (US); Bryan A. Roecklein, Belle Mead, NJ (US); Benjamin Johns, Scotch Plains, NJ (US)

(73) Assignee: Meda Pharmaceuticals Inc., Somerset, NJ (US)

( * ) Notice: Subject to any disclaimer, the term of this patent is extended or adjusted under 35 U.S.C. 154(b) by 535 days.

(21) Appl. No.: 12/529,674

(22) PCT Filed: Mar. 3, 2008

(86) PCT No.: PCT/US2008/002770
§ 371 (c)(1),
(2), (4) Date: Mar. 1, 2010

(87) PCT Pub. No.: WO2008/109018
PCT Pub. Date: Sep. 12, 2008

(65) Prior Publication Data
US 2010/0189782 A1 Jul. 29, 2010

Related U.S. Application Data

(60) Provisional application No. 60/892,805, filed on Mar. 2, 2007.

(51) Int. Cl.
| A61K 9/54 | (2006.01) |
| A61K 31/27 | (2006.01) |
| A61K 9/50 | (2006.01) |
| A61K 45/06 | (2006.01) |

(52) U.S. Cl.
CPC .............. *A61K 9/5084* (2013.01); *A61K 31/27* (2013.01); *A61K 45/06* (2013.01)
USPC ........................................................ 424/458

(58) Field of Classification Search
USPC ........................................................ 424/458
See application file for complete search history.

(56) References Cited

U.S. PATENT DOCUMENTS

| 3,173,876 A | 3/1965 | Zobrist |
| 3,276,586 A | 10/1966 | Rosaen |
| 3,541,005 A | 11/1970 | Strathmann et al. |
| 3,541,006 A | 11/1970 | Bixler |
| 3,546,142 A | 12/1970 | Michaels et al. |
| 3,854,770 A | 12/1974 | Grise et al. |
| 4,077,407 A | 3/1978 | Theeuwes et al. |
| 4,235,236 A | 11/1980 | Theeuwes |
| 4,449,983 A | 5/1984 | Cortese et al. |
| 4,455,143 A | 6/1984 | Theeuwes et al. |
| 4,722,938 A | 2/1988 | Sunshine et al. |
| 4,780,463 A | 10/1988 | Sunshine et al. |
| 4,800,087 A | 1/1989 | Mehta |
| 4,863,742 A | 9/1989 | Panoz et al. |
| 4,874,613 A | 10/1989 | Hsiao |
| 4,923,898 A | 5/1990 | Sunshine et al. |
| 5,026,560 A | 6/1991 | Makino et al. |
| 5,260,337 A | 11/1993 | Sims et al. |
| 5,271,946 A | 12/1993 | Hettche |
| 5,621,005 A | 4/1997 | Gowan, Jr. |
| 5,891,474 A | 4/1999 | Busetti et al. |
| 6,149,941 A | 11/2000 | Schwarz et al. |
| 6,165,512 A | 12/2000 | Mezaache et al. |
| 6,207,197 B1 | 3/2001 | Illum et al. |
| 6,319,513 B1 | 11/2001 | Dobrozsi |
| 6,500,459 B1 * | 12/2002 | Chhabra et al. ............... 424/474 |
| 6,552,024 B1 | 4/2003 | Chen et al. |
| 6,596,298 B2 | 7/2003 | Leung et al. |
| 6,652,881 B2 | 11/2003 | Stamm et al. |
| 6,696,091 B2 | 2/2004 | Thakur et al. |
| 6,984,404 B1 | 1/2006 | Talton et al. |
| 7,037,529 B2 | 5/2006 | Stamm et al. |
| 7,108,865 B2 | 9/2006 | Curatolo et al. |
| 2002/0009496 A1 * | 1/2002 | Stamm et al. .................. 424/490 |
| 2004/0213846 A1 * | 10/2004 | Greenblatt et al. ........... 424/469 |
| 2004/0213848 A1 | 10/2004 | Li et al. |
| 2005/0100594 A1 * | 5/2005 | Sen et al. ...................... 424/458 |

(Continued)

FOREIGN PATENT DOCUMENTS

WO    WO 86/03681 A1    7/1986

OTHER PUBLICATIONS

Dalén, P., et al., "Formation of meprobamate from carisoprodol is catalysed by CYP2C19," *Pharmacogenetics* 6: 387-394, Chapman & Hall (1996).

International Search Report for International Application No. PCT/US08/02770, United States Patent and Trademark Office, Alexandria, Virginia (Jun. 11, 2008).

International Preliminary Examination Report for International Application No. PCT/US2008/002770, The International Bureau of WIPO, Geneva, Switzerland (Sep. 8, 2009) (including Written Opinion dated Jun. 11, 2008).

(Continued)

*Primary Examiner* — Johann R Richter
*Assistant Examiner* — Audrea Buckley
(74) *Attorney, Agent, or Firm* — Sterne, Kessler, Goldstein & Fox P.L.L.C.

(57) ABSTRACT

The present invention provides compositions comprising carisoprodol or pharmaceutically acceptable salts, esters or derivatives thereof. In certain embodiments, the invention provides pharmaceutical compositions comprising the skeletal muscle relaxant carisoprodol and one or more additional active agents, such as one or more nonsteroidal antiinflammatory drugs (NSAIDs). The invention further provides methods of use of such compositions in preventing, alleviating and/or treating musculoskeletal pain, muscle spasms, or other non-malignant painful conditions including methods in which the circulating levels of the active pharmaceutical form of carisoprodol are controlled by use of extended- or controlled-release formulations or by strict control of dosage regimen, so as to reduce the level of somnolence observed with other muscle relaxant compositions.

45 Claims, 6 Drawing Sheets

(56) References Cited

U.S. PATENT DOCUMENTS

2006/0177507 A1* 8/2006 Faour et al. .................. 424/468
2006/0281775 A1 12/2006 Kelly et al.
2007/0020335 A1* 1/2007 Chen et al. .................. 424/486

OTHER PUBLICATIONS

SOMA® (carisoprodol) Tablets, USP, Physician's Desk Reference 59: 1976, Thomson PDR (2005).
"Using Dow Excipients for Controlled Release of Drugs in Hydrophilic Matrix Systems," DOW Chemical Company, Midland, MI, USA, 36 pages (2006), downloaded from http://msdssearch.dow.com/ PublishedLiteratureDOWCOM/dh_0379/0901b803803797ad.pdf?filepath=methocel/pdfs/noreg/198-02075.pdf&fromPage=GetDoc on Jun. 5, 2014.
Chen, R., et al., "Particle Design of Three-Component System for Sustained Release Using a 4-Fluid Nozzle Spray-Drying Technique," *Chem. Pharm. Bull.* 54:1486-1490, Pharmaceutical Society of Japan, Tokyo, Japan (Nov. 2006).
Tayade, P.T. And Kale, R.D., "Encapsulation of Water-Insoluble Drug by a Cross-linking Technique: Effect of Process and Formulation Variables on Encapsulation Efficiency, Particle Size, and In Vitro Dissolution Rate," *AAPS PharmSci.* 6:1-8, American Association of Pharmaceutical Scientists, Arlington, United States (Mar. 2004).

* cited by examiner

Carisoprodol (700mg) vs. Meprobamate Metabolite
(Serum concentrations vs. drowsiness)

Meprobamate (400mg) vs. Meprobamate Metabolite
(Serum concentrations vs. drowsiness)

COMPOSITIONS COMPRISING CARISOPRODOL AND METHODS OF USE THEREOF

BACKGROUND OF THE INVENTION

1. Field of the Invention

The present invention is in the fields of pharmaceuticals, formulations chemistry and pharmacology. The invention generally relates to compositions comprising carisoprodol or pharmaceutically acceptable salts, esters or derivatives thereof. In certain embodiments, the invention provides pharmaceutical compositions comprising the skeletal muscle relaxant carisoprodol and one or more additional active agents selected from the group consisting of at least one non-aspirin non-steroidal antiinflammatory drug (non-aspirin NSAID), one or more muscle relaxing compounds, one or more anxiolytic compounds, one or more narcotic analgesics, one or more non-narcotic analgesics, one or more anticonvulsants, one or more antipsychotics, and one or more antidepressants. In additional embodiments, the invention provides methods of use of such compositions in preventing, alleviating and/or treating musculoskeletal pain, muscle spasms, or other non-malignant painful conditions, including methods in which the circulating levels of the active pharmaceutical form of carisoprodol are controlled by the use of suitable drug delivery systems like immediate release tablets, extended, modified or controlled-release tablets, topicals, transdermals and/or by strict control of dosage regimen. In some embodiments, the invention provides a reduced level of somnolence while maintaining therapeutic efficacy using appropriate amount of drug or reduced frequency of dosing.

2. Related Art

Carisoprodol is a skeletal muscle relaxant. It is indicated as an adjunctive to rest, physical therapy, and other measures for the relief of discomfort associated with acute, painful musculoskeletal conditions. Carisoprodol has the following structure:

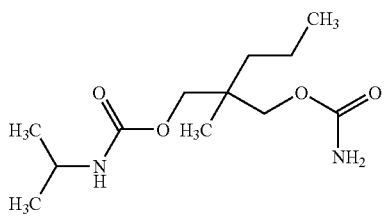 [SMILES: CCCC(C)(COC(N)=O)COC(=O)NC(C)C]

The chemical name for carisoprodol is N-isopropyl-2-methyl-2-propyl-1,3-propanediol dicarbamate, and its molecular formula is $C_{12}H_{24}N_2O_4$.

Carisoprodol is a centrally acting skeletal muscle relaxant that does not directly relax tense skeletal muscles in man. The mode of action of carisoprodol in relieving acute muscle spasm of local origin has not been clearly identified, but may be related to its sedative properties. In animals, carisoprodol has been shown to produce muscle relaxation by blocking interneuronal activity and depressing transmission of polysynaptic neurons in the spinal cord and in the descending reticular formation of the brain. The onset of action is rapid and lasts four to six hours.

Carisoprodol is metabolized in the liver and is excreted by the kidneys. One of the products of metabolism, meprobamate, is active as an anxiolytic. The degree to which it contributes to the efficacy of carisoprodol is unknown.

Carisoprodol is available in 250 mg and 350 mg immediate release tablets (SOMA®, Meda Pharmaceuticals Inc., Somerset, N.J.), in tablets containing a combination of 200 mg carisoprodol and 325 mg aspirin (SOMA® Compound, Meda Pharmaceuticals Inc., Somerset, N.J.) and in tablets containing a combination of 200 mg carisoprodol, 325 mg aspirin and 16 mg codeine phosphate (SOMA® Compound with Codeine CIII, Meda Pharmaceuticals Inc., Somerset, N.J.).

U.S. Pat. Nos. 4,923,898, 4,722,938 and 4,780,463 disclose pharmaceutical analgesic, anti-inflammatory and skeletal muscle relaxant compositions and methods of using same comprising an analgesically and anti-inflammatory effective amount of at least one non-steroidal anti-inflammatory drug other than aspirin, acetaminophen and phenacetin, in combination with an effective amount of a skeletal muscle relaxant.

U.S. Pat. No. 5,260,337 discloses pharmaceutical compositions for use in the treatment of pain and inflammation and the treatment of muscle spasms and associated pain, soreness and tightness of muscles in mammalian organism, the composition comprising: (i) an analgesically and anti-inflammatory effective amount of (S)-ibuprofen, or a salt thereof, substantially free of (R)-ibuprofen; and (ii) an amount effective in the treatment of muscle spasms of at least one of the muscle relaxants, or a therapeutically active stereoisomer thereof, substantially free of its other stereoisomers.

Non-steroidal anti-inflammatory drugs (NSAIDs) are drugs that reduce pain, fever and inflammation. They are used for the treatment of acute or chronic conditions where pain and inflammation are present. NSAIDs are classified as non-selective inhibitors of the enzyme cyclooxygenase, as selective cyclooxygenase-1 (COX-1) inhibitors and selective cyclooxygenase-2 (COX-2) inhibitors. NSAIDs can also be classified based on their chemical structure, including, but not limited to, acetic acid derivatives such as diclofenac, aceclofenac, ketorolac, and propionic acid derivatives such as ibuprofen, flurbiprofen, ketoprofen and naproxen.

Various muscle relaxing compounds other than carisoprodol exist. The skeletal muscle relaxants may act locally on the skeletal muscle or centrally on the central nervous system (CNS). These muscle relaxing compounds may possess mild depressant properties on the CNS. Typical examples of such muscle relaxing compounds include, but are not limited to, mephenesin (MYANESIN®, TOLSEROL®), mephenesin carbamate (TOLSERAM®), mephenesin acid succinate, methocarbamol (DELASIN®, FORBAXIN®), chlorphenesin carbamate (MAOLATE®), mephenoxalone, metaxalone (SKELAXIN®), meprobamate (AMOSENE®, BAMATE®, EQUAGESIC®, EQUANIL®, MEPRIAM®, MEPRO-ASPIRIN®, MICRAININ®, MILPREM-200®, MILPREM-400®, MILTOWN®, NEURAMATE®, PMB 200®, PMB 400®, Q-GESIC®, and TRANMEP®), zoxazolamine (FLEXIN®), chlorzoxazone (PARAFLEX®, PARAFON FORTE DSC®, STRIFON FORTE DSC®), chlordiazepoxide HCl (A-POXIDE®, CHLORDIAZACHEL®, LIBRIUM®, LYGEN®); diazepam (VALIUM®), analexin, baclofen (KEMSTRO®, LIORESAL®), chlormezanone (TRANCOPAL®), cyclobenzaprine HCl (FLEXERIL®), orphenadrine citrate (INVAGESIC®, INVAGESIC FORTE®, NORFLEX®, NORGESIC®, NORGESIC FORTE®, ORPHENGESIC®, ORPHENGESIC FORTE®), alcuronium, atracurium, cisatracurium, dimethyltubocurarine, doxacurium chloride, fazadinium bromide, gallamine, hexafluoronium, mivacurium chloride, pancuronium, pipecuronium bromide, rocuronium bromide, suxamethonium, tubocurarine, vecuronium, febarbamate, phenprobamate, phenyramidol, pridinol, styramate, tetrazepam, thiocolchicoside, tizanidine, tolperisone, and dantrolene.

NAXADOL® (Syntex, S.A. of C.V., Mexico) is a muscle relaxant in the form of capsules containing 250 mg naproxen and 200 mg carisoprodol. It is indicated for the alleviation of musculoskeletal pain.

DOLAREN® (Laboratorios A.F., S.A. of C.V., Mexico) is also indicated for the treatment of musculoskeletal pain and contains 50 mg of diclofenac and 200 mg of carisoprodol.

There exists a need for pharmaceutical compositions containing carisoprodol and one or more additional active agents and treatment methods that relieve musculoskeletal pain with reduced side effects, such as somnolence, and that provide a rapid onset of pain relief. There also exists a need for pharmaceutical compositions that provide a controlled release of carisoprodol, with or without one or more additional active agents, for convenient dosing and more effective treatment of musculoskeletal pain. There also exists a need for pharmaceutical compositions containing carisoprodol with or without one or more additional active agents and treatment methods for topical or transdermal application that relieve musculoskeletal pain with reduced side effects, such as somnolence and that also provide a more effective treatment of musculoskeletal pain.

BRIEF SUMMARY OF THE INVENTION

The present invention provides compositions comprising carisoprodol or pharmaceutically acceptable salts, esters or derivatives thereof, as well as methods for their use and kits containing such pharmaceutical compositions. Some embodiments of the present inventions provide a pharmaceutical composition comprising (or consisting essentially of) a dose of about 250 mg to about 800 mg of carisoprodol (e.g., about 250 mg, about 300 mg, about 400 mg, about 500 mg, about 600 mg, about 700 mg, or about 800 mg), or a pharmaceutically acceptable derivative, salt or ester thereof, and one or more pharmaceutically acceptable carriers or excipients. The pharmaceutical composition of the present invention can further comprise one or more additional active agents selected from a group consisting of: non-aspirin NSAID, one or more muscle relaxing compounds, one or more anxiolytic compounds, one or more narcotic analgesics, one or more non-narcotic analgesics, one or more anticonvulsants, one or more antipsychotics, and one or more antidepressants. Suitably, the compositions of the present invention comprise particles of carisoprodol that are less than about 250 microns in size.

The non-aspirin NSAID can be selected from, but not limited to, the group consisting of diclofenac, aceclofenac, ketorolac, ibuprofen, flurbiprofen, ketoprofen, and naproxen, and pharmaceutically acceptable derivatives, salts or esters thereof. In some embodiments, the non-aspirin NSAID is diclofenac in any pharmaceutically acceptable salt, ester or derivative thereof. In some embodiments, the diclofenac is present to provide a dose of about 50 mg to about 160 mg, about 40 mg to about 100 mg, about 80 mg to about 160 mg, about 50 mg, or about 100 mg by weight of the composition, in a pharmaceutically acceptable derivative.

Suitable muscle relaxing compounds include, but are not limited to, mephenesin (MYANESIN®, TOLSEROL®), mephenesin carbamate (TOLSERAM®), mephenesin acid succinate, methocarbamol (DELASIN®, FORBAXIN®), chlorphenesin carbamate (MAOLATE®), mephenoxalone, metaxalone (SKELAXIN®), meprobamate (AMOSENE®, BAMATE®, EQUAGESIC®, EQUANIL®, MEPRIAM®, MEPRO-ASPIRIN®, MICRAININ®, MILPREM-200®, MILPREM-400®, MILTOWN®, NEURAMATE®, PMB 200®, PMB 400®, Q-GESIC®, and TRANMEP®), zox- azolamine (FLEXIN®), chlorzoxazone (PARAFLEX®, PARAFON FORTE DSC®, STRIFON FORTE DSC®), chlordiazepoxide HCl (A-POXIDE®, CHLORDIAZA-CHEL®, LIBRIUM®, LYGEN®), diazepam (VALIUM®), analexin, baclofen (KEMSTRO®, LIORESAL®), chlormezanone (TRANCOPAL®), cyclobenzaprine HCl (FLEXERIL®), orphenadrine citrate (INVAGESIC®, INVAGESIC FORTE®, NORFLEX®, NORGESIC®, NORGESIC FORTE®, ORPHENGESIC®, ORPHENGESIC FORTE®), alcuronium, atracurium, cisatracurium, dimethyltubocurarine, doxacurium chloride, fazadinium bromide, gallamine, hexafluoronium, mivacurium chloride, pancuronium, pipecuronium bromide, rocuronium bromide, suxamethonium, tubocurarine, vecuronium, febarbamate, phenprobamate, phenyramidol, pridinol, styramate, tetrazepam, thiocolchicoside, tizanidine, tolperisone, and dantrolene.

Suitable anxiolytic compounds include, but are not limited to, benzodiazepines such as lorazepam (Ativan®), alprazolam (Xanax®), and diazepam (Valium®), and non-benzodiazepines such as buspirone (Buspar®), barbiturates and meprobamate (Miltown®), and herbals such as St. John's wort, kava, and bacopa.

Suitable narcotic analgesic compounds include, but are not limited to, anileridine, codeine, hydrocodone, hydromorphone, levorphanol, meperidine, methadone, morphine, oxycodone, pentazocine, propoxyphene, buprenorphine, butorphanol, nalbuphine, opium, and oxymorphone.

Suitable non-narcotic analgesic compounds include, but are not limited to, acetaminophen, ibuprofen, naproxen and tramadol.

In some embodiments of the present invention, the pharmaceutical composition is formulated for oral, topical, transdermal, or parenteral administration.

The present invention also provides a method of treating or preventing musculoskeletal pain or muscle spasm in an animal suffering from or predisposed thereto, comprising administering an effective amount of the composition of the present invention to the animal.

Some embodiments of the present invention provides a method of treating or preventing musculoskeletal pain or muscle spasm in an animal suffering from or predisposed thereto, comprising administering to the animal a pharmaceutical composition comprising about 250 mg of carisoprodol or a pharmaceutically acceptable derivative, salt or ester thereof, wherein the method results in a reduced level of sedation or other central nervous system adverse events experienced by the animal compared to the level of sedation or other central nervous system adverse events experienced by the animal upon administration of a composition comprising about 350 mg of carisoprodol. The pharmaceutical composition used in such a method can further comprise one or more additional active agents selected from the group consisting of non-aspirin NSAID, one or more muscle relaxing compounds, one or more anxiolytic compounds, one or more narcotic analgesics, one or more non-narcotic analgesics, one or more anticonvulsants, one or more antipsychotics, and one or more antidepressants. In some embodiments of the present invention, the animal is a mammal, preferably a mammal, more preferably a human.

The present invention further provides controlled release pharmaceutical formulations suitable for oral administration, comprising carisoprodol or a pharmaceutically acceptable derivative, salt or ester thereof, and a pharmaceutically acceptable matrix adapted to provide a controlled release of carisoprodol or a pharmaceutically acceptable derivative, salt or ester thereof upon oral administration, having a dissolution rate in vitro when measured using (i) Apparatus 2 (paddle)

described in USP 30 at 65 rpm in 1000 mL of 0.1 N hydrochloric acid from 0 hours to 12 hours of dissolution at 37.0±0.5° C. and using high performance liquid chromatography (HPLC) for quantification, or (ii) Apparatus 1 (basket) described in USP 30 at 75 rpm in 1000 ml of 0.1 N hydrochloric acid containing 0.5% sodium lauryl sulfate from 0 hours to 12 hours of dissolution at 37.0±0.5° C. and using high performance liquid chromatography (HPLC) for quantification.

Example of results obtained when using Apparatus 2 (paddles) at 65 rpm is provided below:
between 25 and 70% carisoprodol released in 30 minutes;
between 40 and 80% carisoprodol released in 1 hour;
between 60 and 90% carisoprodol released in 2 hours;
greater than 70% carisoprodol released in 4 hours;
greater than 85% carisoprodol released in 8 hours; and
greater than 95% carisoprodol released in 12 hours,
by weight of the label claim.

The term, "label claim" refers to the drug content reported on the product label as being present in the dosage form. For Example, Soma® 700 mg controlled release tablets will have a label claim of 700 mg carisoprodol per tablet.

The controlled release formulation can further comprise at least one additional active agent selected from the group consisting of one or more non-aspirin NSAID, one or more muscle relaxing compounds, one or more anxiolytic compounds, one or more narcotic analgesics, one or more non-narcotic analgesics, one or more anticonvulsants, one or more antipsychotics, an one or more antidepressants.

The controlled release formulation can be in the form of a capsule filled with a plurality of controlled release pellets (spheroids) comprising coated and uncoated pellets with a controlled release film coat or in the form of a tablet containing carisoprodol incorporated into a controlled release hydrophilic polymer matrix.

The controlled release formulations of the present invention are suitable for dosing every 12 hours or more, such as every 12 or 24 hours.

In some embodiments, the controlled release formulation of the present invention comprises about 250 mg to about 900 mg, about 300 mg to about 900 mg, about 400 mg to about 800 mg, about 500 mg to about 700 mg, or about 700 mg of carisoprodol or a pharmaceutically acceptable derivative, salt or ester thereof.

In some embodiments of the present invention, the controlled release formulation is in the form of a tablet, a capsule, a sachet, containing a plurality of multiparticulates. In some embodiments, the plurality of multiparticulates comprises coated and uncoated granules, spheroids, or pellets of a suitable particle size range. Suitably, the controlled release formulations comprise carisoprodol that has a particle size such that greater than about 30% of the particles are about 150 microns or greater. More suitably, the carisoprodol has a particle size such that greater than about 40% of the particles are about 250 microns or greater.

The present invention also provides a method of treating or preventing musculoskeletal pain or muscle spasm or other non-malignant painful conditions in an animal suffering from or predisposed thereto, comprising administering an effective amount of the controlled release formulations of the present invention to an animal.

The present invention further provides a method of treating or preventing musculoskeletal pain or muscle spasm or other non-malignant painful conditions in an animal suffering from or predisposed thereto, comprising orally administering to the animal a controlled release formulation comprising carisoprodol or a pharmaceutically acceptable derivative, salt or ester thereof, and a pharmaceutically acceptable hydrophilic polymer matrix adapted to provide a controlled release of carisoprodol or a pharmaceutically acceptable derivative, salt or ester thereof upon oral administration, having a dissolution rate in vitro when measured using (i) Apparatus 2 (paddle) described in USP 30 at 65 rpm in 1000 ml 0.1 N hydrochloric acid from 0 hours to 12 hours of dissolution, at 37.0±0.5° C. and using high performance liquid chromatography (HPLC) for quantification or (ii) Apparatus 1 (basket) described in USP 30 at 75 rpm in 1000 ml 0.1 N hydrochloric acid containing 0.5% sodium lauryl sulfate from 0 hours to 12 hours of dissolution at 37.0±0.5° C. and using high performance liquid chromatography (HPLC) for quantification.

Example of results obtained when using Apparatus 2 (paddles) at 65 rpm is provided below:
between 25 and 70% carisoprodol released in 30 minutes;
between 40 and 80% carisoprodol released in 1 hour;
between 60 and 90% carisoprodol released in 2 hours;
greater than 70% carisoprodol released in 4 hours;
greater than 85% carisoprodol released in 8 hours; and
greater than 95% carisoprodol released in 12 hours,
by weight of the label claim.
wherein the method results in a reduced level of sedation experienced by the animal compared to the level of sedation experienced by the animal upon administration of an immediate release dosage form comprising 350 mg of carisoprodol given up to four times per day. The pharmaceutical formulation used in this method can further comprise one or more additional active agents selected from the group consisting of at least one non-aspirin NSAID, one or more muscle relaxing compounds, one or more anxiolytic compounds, one or more narcotic analgesics, one or more non-narcotic analgesics, one or more anticonvulsants, one or more antipsychotics, and one or more antidepressants.

Some embodiments of the present invention provide a method of treating or preventing musculoskeletal pain or muscle spasm or other non-malignant painful conditions in an animal suffering from or predisposed thereto by administering to the animal a therapeutic amount of carisoprodol or a pharmaceutically acceptable derivative, salt or ester thereof, such that the administration results in the maintenance in the plasma of the animal of a therapeutic amount of carisoprodol or a pain- or spasm-treating or -preventing metabolite thereof for a period greater than 12 hours after administration of the carisoprodol or pharmaceutically acceptable derivative, salt or ester thereof and such that the musculoskeletal pain or muscle spasm or other non-malignant painful condition is treated or prevented in the animal and the animal experiences a reduced level of sedation compared to the level of sedation experienced by the animal upon administration of an immediate release dosage form comprising 350 mg of carisoprodol given four times per day.

In certain such embodiments, the method comprises administering to the animal a pharmaceutical composition comprised of (or consists essentially of) a therapeutic amount of carisoprodol, or a pharmaceutically acceptable derivative, salt or ester thereof, and one or more pharmaceutically acceptable carriers or excipients. In such methods, the composition may further comprise one or more additional active agents selected from the group consisting of at least one non-aspirin NSAID, one or more muscle relaxing compounds, one or more anxiolytic compounds, one or more narcotic analgesics, one or more non-narcotic analgesics, one or more anticonvulsants, one or more antipsychotics, and one or more antidepressants.

In some embodiments, a controlled release composition of the present invention is administered to the animal one or two times per day. In some embodiments, an immediate release composition of the present invention is administered to the animal four times per day.

Certain embodiments of the present invention provide a method of treating or preventing musculoskeletal pain or muscle spasm or other non-malignant painful conditions in an animal suffering from or predisposed thereto by administering to the animal a therapeutic amount of carisoprodol or a pharmaceutically acceptable derivative, salt or ester thereof, such that the administration results in the maintenance in the blood circulation of the animal of a therapeutic amount of carisoprodol or a pain- or spasm-treating or -preventing metabolite thereof from between 0.5 hours and 24 hours, preferably greater than 12 hours after administration of the carisoprodol or pharmaceutically acceptable derivative, salt or ester thereof and such that the musculoskeletal pain or muscle spasm or other non-malignant painful condition is treated or prevented in the animal and the animal experiences a reduced level of sedation compared to the level of sedation experienced by the animal upon administration of an immediate release composition comprising 350 mg of carisoprodol given up to four times per day. In certain such embodiments, the method comprises administering to the animal a controlled release pharmaceutical formulation comprising carisoprodol or a pharmaceutically acceptable derivative, salt or ester thereof, and a pharmaceutically acceptable hydrophilic matrix adapted to provide a controlled release of carisoprodol or a pharmaceutically acceptable derivative, salt or ester thereof upon administration. In certain specific embodiments according to this aspect of the invention, the compositions used in such methods have a dissolution rate in vitro of the following, when measured using (i) Apparatus 2 (paddle) described in USP 30 at 65 rpm in 1000 mL of 0.1 N hydrochloric acid from 0 hours to 12 hours of dissolution, at 37.0±0.5° C. and using high performance liquid chromatography (HPLC) for quantification or (ii) Apparatus 1 (basket) described in USP 30 at 50 rpm in 1000 ml of 0.1 N hydrochloric acid containing 0.5% sodium lauryl sulfate from 0 hours to 12 hours of dissolution at 37.0±0.5° C. and using high performance liquid chromatography (HPLC) for quantification:

Example of results obtained when using Apparatus 2 (paddle) at 65 rpm is provided below:
 between 25 and 70% carisoprodol released in 30 minutes;
 between 40 and 80% carisoprodol released in 1 hour;
 between 60 and 90% carisoprodol released in 2 hours;
 greater than 70% carisoprodol released in 4 hours;
 greater than 85% carisoprodol released in 8 hours; and
 greater than 95% carisoprodol released in 12 hours,
 all by weight of the label claim.

In certain such methods, the pharmaceutical formulations are formulated for oral administration, e.g., in the form of tablets, capsules, pills, and the like, and other formulations and dosage forms suitable for oral administration that will be familiar to those of ordinary skill. In other such methods, the pharmaceutical formulations are formulated in a manner suitable for administration by other modes of administration that will be familiar to those of ordinary skill in the art, such as those specified elsewhere herein.

The pharmaceutical formulations used in such methods can further comprise one or more additional active agents selected from the group consisting of at least one non-aspirin NSAID, one or more muscle relaxing compounds, one or more anxiolytic compounds, one or more narcotic analgesics, one or more non-narcotic analgesics, one or more anticonvulsants, one or more antipsychotics, and one or more antidepressants.

The present invention further provides a pharmaceutical composition comprising carisoprodol, or a pharmaceutically acceptable derivative, salt or ester thereof, and one or more additional active agents selected from the group consisting of non-aspirin NSAIDs, one or more muscle relaxing compounds, and one or more anxiolytic compounds, one or more narcotic analgesics, one or more non-narcotic analgesics, one or more anticonvulsants, one or more antipsychotics, and one or more antidepressants, wherein the pharmaceutical composition provides for controlled and/or extended release of the carisoprodol or the one or more additional active agents, or both the carisoprodol and the one or more additional active agents from the pharmaceutical composition for a period of about 12 hours to about 24 hours or about 6 hours to about 24 hours.

In some embodiments, the pharmaceutical composition provides for controlled and/or extended release of the carisoprodol or the one or more additional active agents, or both the carisoprodol and the one or more additional active agents from the pharmaceutical composition for a period of about 12 to 24 hours.

In some embodiments, the pharmaceutical composition provides for controlled and/or extended release of carisoprodol, or a pharmaceutically acceptable derivative, salt or ester thereof, without providing for controlled and/or extended release of the one or more additional active agents.

In some embodiments, the pharmaceutical composition provides for controlled and/or extended release of carisoprodol, or a pharmaceutically acceptable derivative, salt or ester thereof, and one or more additional active agents selected from the group consisting of non-aspirin NSAIDs, one or more muscle relaxing compounds, and one or more anxiolytic compounds, one or more narcotic analgesics, one or more non-narcotic analgesics, one or more anticonvulsants, one or more antipsychotics, and one or more antidepressants.

In some embodiments, the pharmaceutical composition provides for controlled and/or extended release of the one or more additional active agents, without providing extended release of carisoprodol, or a pharmaceutically acceptable derivative, salt or ester thereof.

The pharmaceutical compositions of the present invention can comprise about 300 mg to about 900 mg, about 400 mg to about 800 mg, or about 500 mg to about 700 mg, or about 700 mg of carisoprodol, or a pharmaceutically acceptable derivative, salt or ester thereof.

In some embodiments, the pharmaceutical composition is in the form of a tablet comprising:
 i) carisoprodol, or both the carisoprodol and the one or more additional active agents; and
 ii) at least one functional ingredient which provides for controlled and/or extended release of the carisoprodol alone or both the carisoprodol and the one or more additional active agents for a period of up to about 12 hours or up to about 24 hours.

In some embodiments, the pharmaceutical composition is in the form of a tablet and the carisoprodol or the one or more additional active agents, or both the carisoprodol and the one or more additional active agents is bound to at least one ion exchange resin and provides controlled and/or extended release of the carisoprodol or the one or more additional active agents, or both the carisoprodol and the active agent for a period of greater than about 12 hours.

In some embodiments, the pharmaceutical composition is in the form of a tablet and the carisoprodol or the one or more additional active agents, or both the carisoprodol and the one or more additional active agents are embedded in a matrix which provides controlled and/or extended release of the carisoprodol or the one or more additional active agents, or both the carisoprodol and the additional active agent for a period greater than about 12 hours.

The present invention also provides a pharmaceutical composition combining a rapid initial release with extended release of carisoprodol, the composition comprising:

(i) an extragranular phase containing carisoprodol or a pharmaceutically acceptable derivative, salt or ester thereof for rapid initial release:

(ii) an intragranular phase containing carisoprodol or a pharmaceutically acceptable derivative, salt or ester thereof granulated with a controlled release hydrophilic polymer for a extended release;

wherein a suitable particle size range of carisoprodol is selected for intragranular or extragranular incorporation for the desired release;

wherein a suitable viscosity range of the hydrophilic polymer is selected for the desired release; and (iii) conventional pharmaceutically acceptable excipients selected from the group consisting of disintegrants, binders, fillers and lubricants and combinations thereof;

wherein the composition provides extended release of carisoprodol from the composition for a period greater than 12 hours.

The rapid onset formulations of the present invention can further comprise one or more additional active agents selected from the group consisting of non-aspirin NSAIDs, one or more muscle relaxing compounds, and one or more anxiolytic compounds, one or more narcotic analgesics, one or more non-narcotic analgesics, one or more anticonvulsants, one or more antipsychotics, and one or more antidepressants.

In some embodiments, the pharmaceutical composition provides for rapid initial release and extended release of the one or more additional active agents for a period greater than 12 hours.

In some embodiments, the pharmaceutical composition provides controlled release consisting of rapid initial release and extended release of carisoprodol with or without the one or more additional active agents for about 6 hours to about 24 hours, preferably a period greater than 12 hours in the form of a bilayer tablet, where one layer comprises the immediate release formulation and the other layer provides the extended release formulation.

The present invention further provides a pharmaceutical composition comprising carisoprodol, or a pharmaceutically acceptable derivative, salt or ester thereof, wherein the pharmaceutical composition produces a reduced level of somnolence when administered to an animal, as measured by standardized tests for measuring somnolence or drowsiness in clinical studies. For example, it is contemplated that the pharmaceutical composition of the present invention produces somnolence or drowsiness in less than about 25%, less than about 20%, less than about 15%, or less than about 10% of animals to which it is administered, compared to placebo, as measured by spontaneous reporting of experiences during a randomized, double blind, placebo controlled study.

Some embodiments of the present invention provide a method of treating or preventing musculoskeletal pain or muscle spasm or other non-malignant painful conditions in an animal suffering from or predisposed thereto, comprising administering to the animal a pharmaceutical composition comprising about 30 mg to about 300 mg, about 50 mg to about 290 mg, about 100 mg to about 280 mg, about 150 mg to about 270 mg, or about 250 mg of carisoprodol, or a pharmaceutically acceptable derivative, salt or ester thereof, at least 3 times daily. In some embodiments, such method results in a reduced level of sedation experienced by the animal compared to the level of sedation experienced by the animal upon administration of an immediate release composition comprising 350 mg of carisoprodol, given four times per day. In some embodiments, such a treatment method is carried out by orally administering the pharmaceutical compositions of the present invention. The pharmaceutical composition can further comprise one or more additional active agents selected from the group consisting of non-aspirin NSAIDs, one or more muscle relaxing compounds, and one or more anxiolytic compounds, one or more narcotic analgesics, one or more non-narcotic analgesics, one or more anticonvulsants, one or more antipsychotics, and one or more antidepressants.

The present invention also provides a kit for treating or preventing musculoskeletal pain or muscle spasm in an animal suffering from or predisposed thereto, comprising at least 3 oral dosage forms for each day of treating or preventing musculoskeletal pain or muscle spasm in the animal, wherein each oral dosage form comprises about 30 mg to about 300 mg, about 50 mg to about 290 mg, about 100 mg to about 280 mg, about 150 mg to about 270 mg, or about 250 mg of carisoprodol, or a pharmaceutically acceptable derivative, salt or ester thereof, and a carrying component housing the oral dosage forms, wherein the carrying component indicates the time of day each dosage form should be administered to the animal. The oral dosage forms can further comprise one or more additional active agents selected from the group consisting of non-aspirin NSAIDs, one or more muscle relaxing compounds, and one or more anxiolytic compounds, one or more narcotic analgesics, one or more non-narcotic analgesics, one or more anticonvulsants, one or more antipsychotics, and one or more antidepressants. In some embodiments, the carrying component further comprises an alarm which provides a signal at a time when the dosage form should be administered to the animal.

Other features and advantages of the invention will be apparent from the following detailed description, and from the claims. The disclosed materials, methods, and examples are for illustrative purposes only and are not intended to be limiting. Skilled artisans will appreciate that methods and materials similar or equivalent to those described herein can be used to practice the invention.

Unless otherwise defined, all technical and scientific terms used herein have the meaning commonly understood by one skilled in the art to which this invention belongs. All publications, patent applications, patents, and other references mentioned herein are incorporated by reference in their entirety. In case of conflict, the present specification, including definitions, will control.

BRIEF DESCRIPTION OF THE DRAWINGS/FIGURES

DETAILED DESCRIPTION OF THE INVENTION

Overview

Figure 1:
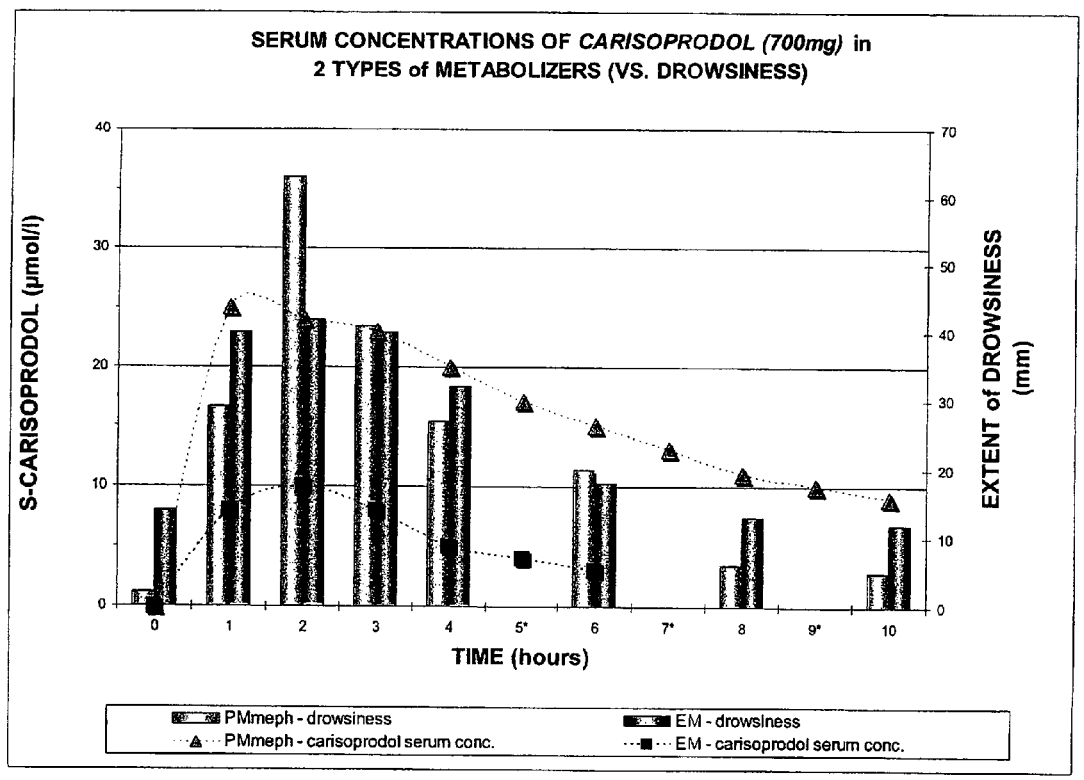
FIG. 1 shows a graph of the serum concentrations of carisoprodol (700 mg) in 2 types of metabolizers over time (versus drowsiness).

The present invention provides pharmaceutical compositions comprising carisoprodol, or a pharmaceutically acceptable derivative, salt or ester thereof, and one or more pharmaceutically acceptable carriers or excipients. Racemic (i.e., enantiomeric) forms and polymorphic forms of carisoprodol can also be suitably used in the present invention. In some embodiments, the present invention provides pharmaceutical compositions comprising carisoprodol and one or more additional active agents selected from a group consisting of one or more non-aspirin NSAIDs, one or more muscle relaxing compounds, one or more anxiolytic compounds, one or more narcotic analgesics, one or more non-narcotic analgesics, one or more anticonvulsants, one or more antipsychotics, and one or more antidepressants.

The present invention further provides methods of use of such compositions in preventing, alleviating and/or treating musculoskeletal pain, muscle spasm, or other non-malignant painful conditions, including methods in which the plasma levels of the active pharmaceutical form of carisoprodol are controlled by the use of controlled-release formulations or by strict control of dosage regimen, so as to reduce the level of somnolence and other CNS adverse events observed with other muscle relaxant compositions.

As used herein when referring to any numerical value, the term "about" means a value falling within a range that is ±10% of the stated value. For example, "about 50° C." encompasses a range of temperatures from 45° C. to 55° C., inclusive; similarly, "about 100 mM" encompasses a range of concentrations from 90 mM to 110 mM, inclusive.

As used herein, the articles "a," "an" and "one" mean "at least one" or "one or more" of the object to which they refer, unless otherwise specified or made clear by the context in which they appear herein.

Compositions and Modes of Administration

In certain embodiments, the invention provides compositions, particularly pharmaceutical compositions, comprising (or consisting essentially of) a therapeutically or pharmacologically effective amount of carisoprodol or a pharmaceutically acceptable salt or ester thereof and one or more pharmaceutically acceptable carriers or excipients. By "pharmaceutically acceptable carrier or excipient" is meant a non-toxic solid, semisolid or liquid filler, diluent, encapsulating material or formulation auxiliary of any type.

The compositions of the present invention can be administered to a patient via any suitable mode of administration, including oral, buccal, sublingual, topical, parenteral (subcutaneous, intramuscular, intravenous, intraarticular, or intrathecally), and transdermal. In some embodiments of the present invention, the extended release solid oral compositions provided by the present invention suitably comprise from about 250 mg to about 900 mg, about 300 mg to 900 mg, about 400 to about 800 mg, about 500 mg to about 700 mg, or about 700 mg, of carisoprodol, or a pharmaceutically acceptable derivative, salt or ester thereof, as the active agent.

In certain embodiments, the compositions of the invention may be formulated into forms for oral administration, including solid dosage forms or liquid dosage forms or sterile liquid forms for injection or semisolid dosage forms for topical administration. In alternative embodiments, the compositions of the invention may be formulated into forms for direct administration to the mucosa, including buccal mucosa (i.e., buccal administration) or oral mucosa under the tongue (i.e., sublingual administration).

Solid dosage forms for oral administration include capsules, tablets, pills, powders, particles and granules. In such solid dosage forms, the active carisoprodol compound(s) are mixed with at least one pharmaceutically acceptable excipient or carrier such as (a) fillers or extenders such as starches, lactose, sucrose, glucose, mannitol, dicalcium or tricalcium phosphate and microcrystalline cellulose or silicified microcrystalline cellulose; (b) binders such as hypromellose, sodium carboxymethylcellulose, alginates, gelatin, polyvinylpyrrolidone, and acacia; (c) disintegrating agents such as agar-agar, calcium carbonate, potato or tapioca starch, alginic acid, certain silicates, sodium carboxymethyl cellulose, pregelatinized starch and sodium starch glycolate; (d) lubricants such as calcium stearate, magnesium stearate, stearic acid, solid polyethylene glycols, sodium lauryl sulfate, and mixtures thereof; and/or (e) glidants such as talc, silicon dioxide and starch. In the case of capsules, tablets and pills, the dosage form may also comprise buffering agents. Solid compositions of a similar type may also be employed as fillers in soft and hard filled gelatin capsules using such excipients as lactose or milk sugar as well as high molecular weight polyethylene glycols, oils and the like. The solid dosage forms of tablets, dragees, capsules, pills, and granules can be prepared with coatings, which may in themselves provide taste-masking, and shells such as enteric coatings and other coatings that are well known in the pharmaceutical formulating art. The solid dosage forms also may optionally contain opacifying, coloring and/or flavoring agents, and can also be formulated such that they release the entire amount or a portion of the active carisoprodol agent(s) in a desired controlled and/or extended release profile, or preferentially, in a certain part of the intestinal tract, or optionally in a delayed manner (see U.S. Pat. No. 5,271,946, the disclosure of which is incorporated herein by reference in its entirety). Examples of embedding compositions which can be used include polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, elixirs, or sterile liquids for injection. In addition to the active carisoprodol compound, the liquid dosage forms may contain inert diluents and/or solvents commonly used in the art. For example, water or combinations of water with other physiologically acceptable solvents as required are satisfactory for use. Other solvents, solubilizing agents and emulsifiers suitable for use in place of, or in addition to, water include but are not limited to saturated aliphatic mono- and polyvalent alcohols which contain 2-6 carbon atoms (including, but not limited to, ethanol, 1,2-propylene glycol, sorbitol, and glycerine), polyglycols such as polyethylene glycols, and surfactants/emulsifiers like the fatty acid esters of sorbitan, and mixtures thereof. Oils, in particular, cottonseed, peanut, or corn oils, may also be added to the compositions. Besides inert diluents, the oral compositions can also include adjuvants such as wetting agents, emulsifying and suspending agents (e.g., microcrystalline cellulose, sodium carboxymethyl cellulose, hypromellose, carbopol and the like), surfactants, sweetening, flavoring, and perfuming agents, including those described in further detail herein below. Liquid dosage forms that provide the active agent in suspension may comprise, in addition to the active carisoprodol compound, one or more suspending agents such as microcrystalline cellulose, magnesium aluminum silicate, bentonite, agar-agar, hypromellose, sodium carboxymethyl cellulose, carbopol/carbomer, pectin, acacia, tragacanth or their mixtures.

Certain compositions of the invention may further comprise one or more solubility-enhancing agents that are used to improve the solubility of the carisoprodol, especially in the lower regions of the gastro intestinal tract. Solubility-enhancing agents that are suitable for use in the compositions of the invention include, but are not limited to, polyvinylpyrrolidone (preferably grades 25, 30, 60, or 90), poloxamer, polysorbate 80, sorbitan monooleate 80, sodium lauryl sulfate, cyclodextrins and polyethylene glycols (molecular weights of 200 to 600).

It is desirable that the compositions of the present invention that are to be administered in liquid form have a pH of about 4.5 to about 7.4, and preferably have a pH of about 5.5 to 7.4, for physiological reasons. Accordingly, in additional embodiments, the compositions of the invention may further comprise one or more buffering agents or combinations thereof, that are used to adjust and/or maintain the compositions into the desired pH range. Adjustment of pH or buffering agents that are suitable for use in the compositions of the invention include, but are not limited to, citric acid, sodium citrate, sodium phosphate (dibasic, heptahydrate form), and TRIS or equivalent conventional buffers, or combinations thereof. The appropriate amounts of buffers and buffering agents, or combinations thereof, that are to be used in the compositions of the invention are readily determined by those of ordinary skill without undue experimentation, particularly in view of the guidance contained herein and in standard formularies such as the United States Pharmacopoeia, *Remington: The Science and Practice of Pharmacy*, and the like, the disclosures of which are incorporated herein by reference in their entireties.

In certain embodiments, the oral liquid formulations of the invention further comprise one or more taste-masking agents, one or more flavoring agents, and/or one or more sweetening agents, or a combination of such agents. Non-limiting examples of such substances include sucralose (about 0.001 to about 1%), sucrose (about 0.5 to about 10%), saccharin (including the salt forms: sodium, calcium, etc.) (about 0.01 to about 2%), fructose (about 0.5 to about 10%), dextrose (about 0.5 to about 10%), corn syrup (about 0.5 to about 10%), aspartame (about 0.01 to about 2%), acesulfame-K (about 0.01 to about 2%), xylitol (about 0.1 to about 10%), sorbitol (about 0.1 to about 10%), erythritol (about 0.1 to about 10%), ammonium glycyrrhizinate (about 0.01 to about 4%), thaumatin (Talin™) (about 0.01 to about 2%), neotame (about 0.01 to about 2%) mannitol (about 0.5 to about 5%), menthol (about 0.01 to about 0.5%), eucalyptus oil (about 0.01 to about 0.5%), camphor (about 0.01 to about 0.5%), natural and/or artificial flavors such as Artificial Custard Cream Flavor #36184 from International Flavors and Fragrances, Inc. (New York, N.Y.) (about 0.01 to about 1.0%), and the like. Sucralose, an intense sweetener marketed for food and beverage use as SPLENDA® by McNeil Nutritionals LLP (Fort Washington, Pa.), is especially effective as a sweetening and taste-masking agent in the compositions of the present invention, particularly when used at concentrations of from about 0.001% to about 1%, preferably at concentrations of from about 0.01% to about 0.5%, and more preferably at concentrations of from about 0.02% to about 0.2%, and most preferably from about 0.05% to about 0.15% (e.g., about 0.05%, about 0.06%, about 0.07%, about 0.08%, about 0.09%, about 0.10%, about 0.11%, about 0.12%, about 0.13%, about 0.14%, or about 0.15%), of the total composition. Sucralose has been shown to be useful as a taste modifying agent in oral delivery of certain pharmaceutical compositions, for example in sore throat spray products (see U.S. Pat. No. 6,319,513), oral suspensions (see U.S. Pat. Nos. 5,658,919 and 5,621,005), solid dosage forms (see U.S. Pat. No. 6,149,941), quick melt dosage forms (see U.S. Pat. No. 6,165,512) and mucosal delivery (see U.S. Pat. No. 6,552,024). Additional such compositions of the invention may comprise one or more additional taste-masking or flavoring agents such as those described herein, for example menthol at a concentration of from about 0.01% to about 1%, preferably at a concentration of from about 0.05% to about 0.1%. Suitable compositions of the invention include, for example, about 10% to about 90% carisoprodol and about 0.05%-0.15% sucralose, for example, about 20% to about 80% carisoprodol and about 0.05%-0.15% sucralose, or about 30% to about 70% carisoprodol and about 0.05%-0.15% sucralose, or about 40% to about 60% carisoprodol and about 0.15% sucralose, or about 50% carisoprodol and about 0.15% sucralose.

The compositions of the present invention that are provided in aqueous solution form may be preserved for multiple dosing.

Compositions Comprising One or More Additional Active Agents

In addition to carisoprodol and the various excipients disclosed herein, the pharmaceutical compositions of the invention can further comprise (or consist essentially of) one or more additional active agents selected from the group consisting of non-aspirin NSAID, one or more muscle relaxing compounds, one or more anxiolytic compounds, one or more narcotic analgesics, one or more non-narcotic analgesics, one or more anticonvulsants, one or more antipsychotics, and one or more antidepressants.

Any non-aspirin NSAID could be selected in the practice of the present invention. Useful non-aspirin NSAIDs in the compositions and methods of use of the present invention may be selected from any of the following categories:

(1) the propionic acid derivatives or 2-arylpropionic acids (profens);
(2) the acetic acid derivatives or arylalkanoic acids;
(3) the fenamic acid derivatives or N-Arylanthranilic acids (fenamates);
(4) the biphenylcarboxylic acid derivatives;
(5) the enolic acid derivatives (oxicams);
(6) the pyrazolidine derivatives;
(7) the coxibs; and
(8) the sulphonanilides.

The propionic acid derivatives or 2-arylpropionic acids (profens) for use herein include, but are not limited to, ibuprofen, naproxen, benoxaprofen, naproxen sodium, flurbiprofen, fenoprofen, fenbufen, ketoprofen indoprofen, pirprofen, carprofen, oxaprozin, pranoprofen, microprofen, tioxaprofen, suprofen, alminoprofen, tiaprofenic acid, fluprofen, loxoprofen, bucloxic acid, and tiaprofenic acid. Structurally related propionic acid derivatives having similar analgesic and anti-inflammatory properties can also be used in the present invention. Representative members of the propionic acid group include ibuprofen, naproxen, flurbiprofen, fenbufen, fenoprofen, ibuprofen aluminum, ketoprofen, fluprofen and bucloxic acid.

The acetic acid derivatives or arylalkanoic acids for use herein include, but are not limited to, diclofenac, aceclofenac, indomethacin, sulindac, tolmetin, fenclofenac, alclofenac, ibufenac, isoxepac, furofenac, tiopinac, zidometacin, acemetacin, fentiazac, clidanac, oxepinac, bromfenac, etodolac, ketorolac, nabumetone, and sulindac. Structurally related acetic acid derivatives having similar analgesic and anti-inflammatory properties can also be used in the present invention. Representative members of the acetic acid group include tolmetin, ketorolac, sulindac, indomethacin, diclofenac, alclofenac, fenclozic acid and ibufenac.

The fenamic acid derivatives or N-arylanthranilic acids for use herein include, but are not limited to, mefenamic acid, meclofenamic acid, flufenamic acid, niflumic acid and tolfenamic acid. Structurally related fenamic acid derivatives having similar analgesic and anti-inflammatory properties can also be used in the present invention. Representative members of the fenamic acid group include mefenamic acid, meclofenamate sodium (meclofenamic acid, sodium salt) and flufenamic acid.

The biphenylcarboxylic acid derivatives for use herein include, but are not limited to, diflunisal and flufenisal. Structurally related biphenylcarboxylic acid derivatives having similar analgesic and anti-inflammatory properties can also be used in the present invention. Representative members of this group are diflunisal and flufenisal The enolic acid derivatives (oxicams) for use herein include, but are not limited to, piroxicam, sudoxicam, isoxicam, lornoxicam, meloxicam, tenoxicam, and CP-14,304. Structurally related oxicams having similar analgesic and anti-inflammatory properties can also be used in the present invention.

The pyrazolidine derivatives for use herein include, but are not limited to, phenylbutazone, azapropazone, metamizole, and oxyphenbutazone. Structurally related pyrazolidine derivatives having similar analgesic and anti-inflammatory properties can also be used in the present invention.

The coxibs including, but not limited to, celecoxib, etoricoxib, lumiracoxib, parecoxib, rofecoxib (withdrawn from market), and valdecoxib (withdrawn from market).

The sulphonanilides including, but not limited to, nimesulide and others such as licofelone, and omega-3 fatty acids.

In some embodiments of the present invention, the non-aspirin NSAIDs suitable for inclusion in the present compositions include, but are not limited to, diclofenac, aceclofenac, ibuprofen, naproxen, etodolac, flurbiprofen, fenoprofen, ketoprofen, suprofen, fenbufen, fluprofen, tolmetin sodium, oxaprozin, zomepirac, sulindac, indomethacin, piroxicam, mefenamic acid, nabumetone, meclofenamate sodium, diflunisal, flufenisal, piroxicam, ketorolac, sudoxicam and isoxicam.

In further embodiments of the present invention, the non-aspirin NSAID is selected from the group consisting of diclofenac, ketorolac, aceclofenac, ibuprofen and naproxen, and pharmaceutically acceptable derivatives, salts or esters thereof.

Any skeletal muscle relaxant is useful in the practice of the present invention. Useful skeletal muscle relaxants in the present invention include, but are not limited to, glycerylmonoethers and derivatives, oxazoles, substituted alkanediols, benzazoles, and benzodiazepines.

The formulations of the present invention may comprise, in addition to carisoprodol, other muscle relaxing compounds. Typical examples of muscle relaxing compounds include, but are not limited to, mephenesin, mephenesin carbamate, mephenesin acid succinate, methocarbamol, chlorphenesin carbamate, mephenoxalone and metaxalone, meprobamate, zoxazolamine, chlorzoxazone, chlordiazepoxide HCl, diazepam, analexin, baclofen, chlormezanone, cyclobenzaprine HCl, orphenadrine citrate, alcuronium, atracurium, cisatracurium, dimethyltubocurarine, doxacurium chloride, fazadinium bromide, gallamine, hexafluoronium, mivacurium chloride, pancuronium, pipecuronium bromide, rocuronium bromide, suxamethonium, tubocurarine, vecuronium, febarbamate, phenprobamate, phenyramidol, pridinol, styramate, tetrazepam, thiocolchicoside, tizanidine, tolperisone, and dantrolene.

The concentrations, absolute amounts and relative amounts (i.e., relative to the concentration or absolute amount of carisoprodol or a salt or ester thereof) of the additional one or more active agents can vary based on different factors, such as the needs of the patient, the relative potency of the one or more additional active agents, and the rate of release of the active agent. For example, the amounts of one or more additional active agents (e.g., NSAIDs, muscle relaxing compounds, etc), can be present in any amount, for example about 0.01% to about 99% (e.g., about 0.01%, about 0.1%, about 1%, about 10%, about 20%, about 30%, about 40%, about 50%, about 60%, about 70%, about 80%, or about 90%).

In some embodiments of the present invention, the pharmaceutical composition can be in the form of a tablet and can comprise from about 10% to about 90%, about 20% to about 90%, about 30% to about 90%, or about 40% to about 80% by weight of carisoprodol, or a pharmaceutically acceptable salt or ester thereof. In some embodiments, the pharmaceutical composition further comprises one or more additional active agents in an amount from about 0.01 to about 0.25 parts, from about 0.01 to about 0.20 parts, or from about 0.01 to about 0.15 parts of the carisoprodol by weight. The pharmaceutical composition can further comprise about 10% to about 50%, about 20% to about 40%, about 15% to about 35% by weight of pharmaceutically acceptable excipients or carriers.

Chewable and/or Orally Dissolving Formulations

Chewable Formulations

In addition to the solid dosage forms disclosed throughout, the present invention also provides chewable oral formulations. In certain such embodiments, the formulations will comprise (or consist essentially of) an effective amount of carisoprodol along with suitable excipients that allow the formulations to be chewed by the patient. In additional embodiments, the formulations can further comprise one or more taste-masking or sweetening agents, such as those described herein. In one embodiment, sucralose is used in the chewable formulations. One or more additional active agents, such as those described herein, can also optionally be added to the chewable formulations. The amounts of carisoprodol, other optional active agents, and sweetening agents (e.g., sucralose) in the chewable formulations of the present invention are readily determinable by those of ordinary skill in the art, and include those amounts and combinations described herein. Such chewable formulations are especially useful in patient populations where compliance is an issue, such as children, the elderly, and patients who may have difficulty swallowing conventional solid oral dosage forms.

The formulations may also contain colorants to improve the appearance of the chewable formulations. The relative amounts of the colorants selected will vary depending upon the particular hue of the individual colorants and the resultant color desired.

Any standard pharmaceutically acceptable excipient can be used in the chewable tablet formulations which provides adequate compression such as diluents (e.g., mannitol, xylitol, maltitol, lactitol, sorbitol, lactose, sucrose, sucralose, and compressible sugars such as DiPac® (dextrinized sucrose), available from Austin Products Inc. (Holmdel, N.J.), binders, disintegrants, splitting or swelling agents (e.g., polyvinyl polypyrrolidone, croscarmellose sodium (e.g., Ac-Di-Sol available from FMC BioPolymer, Philadelphia, Pa.), starches and derivatives, cellulose and derivatives, microcrystalline celluloses, such as Avicel™ PH 101 or Avicel™ CE-15 (a microcrystalline modified with guar gum), both available from FMC BioPolymer, (Philadelphia, Pa.), lubricating agents (e.g., magnesium stearate), and flow agents (e.g., colloidal silicon dioxide, such as Cab-O-Sil M5® available from Cabot Corporation, Kokomo, Ind.).

Suitable amounts of sweetener (e.g., sucralose, sorbitol, mannitol, etc.) used in the chewable formulations, will be familiar to, and can be readily determined by, those skilled in the art. In certain embodiments, the sweetener is present in an amount from about 0.05% to about 5.0% (e.g., about 0.05%, about 0.1%, about 0.125%, about 0.15%, about 0.2%, about 0.3%, about 0.4%, about 0.5%, about 0.6%, about 0.7%, about 0.8%, about 0.9%, about 1%, about 1.25% about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75% or about 5%). Those of ordinary skill in the art will appreciate that the amount of sweetener may vary depending on the strength of the particular sweetener used and the levels approved by the regulatory authorities for use in pharmaceutical products.

Suitable cyclodextrins for use in the chewable formulations of the present invention include α, β, or γ cyclodextrins, or an alkylated or hydroxyalkylated derivatives thereof, such as heptakis (2,6-di-o-methyl)-β-cyclodextrin (DIMEB), randomly methylated β-cyclodextrin (RAMEB), and hydroxypropyl β-cyclodextrin (HPβCD). A suitable cyclodextrin is β-cyclodextrin (available from Cerestar USA, Inc., Hammond, Ind. or from Roquette America, Inc., Keokuk. Ia. under the trade name Kleptose™). If desired, the complex of the active substance with cyclodextrin can be prepared in advance, for example, by malaxating or granulating the carisoprodol and any additional active substance(s) and the cyclodextrin in the presence of water, or by preparing an aqueous solution containing the carisoprodol and any additional active substance(s) and the cyclodextrin in the desired molar ratio. Alternatively, the carisoprodol and any additional active substance(s) and the cyclodextrin can be simply mixed with other excipients and adjuvants. The molar ratio of the carisoprodol and any additional active substance(s) to cyclodextrin is suitably from about 1.0:1.0 to about 4.0:1.0.

A typical manufacturing process for making either a single layer or bi-layer chewable tablet generally involves blending of the desired agents to form a uniform distribution of the carisoprodol (and any other active agent(s)), excipients (e.g., colorants and flavoring agents as well as others). If desired, an inclusion complex of the carisoprodol and any other active agent(s) and cyclodextrin (e.g., β-cyclodextrin) may be formed prior to blending into the mixture by malaxating the carisoprodol and any other active agent(s) and cyclodextrin in the presence of water in a planetary mixer for about 20 minutes. The mixture is then dried in a drying oven. After drying, the complex is mixed with any color/flavoring blend. The blend is then compressed into a single layer or bi-layer tablet using standard methods well-known to those skilled in the art (e.g., using Kilian, Mannesty press or Courtoy rotary bi-layer tablet press). The colorants and flavoring agents may be added to one or both layers to form a distinctive presentation of the tablet. Methods for preparation of chewable tablets and various components for use in the tablets can be found throughout the detailed description section and the Examples of U.S. Patent Publication No. 2003/0215503, the disclosure of which is incorporated by reference herein for all purposes. Additional chewable/orally dissolving tablets, and methods for their manufacture, are disclosed in U.S. Patent Publication No. 2004/0265372 and U.S. Pat. No. 6,270,790, the disclosures of each of which are incorporated by reference herein for all purposes.

Some embodiments of the present invention provides a palatable chewable tablet comprising (a) about 100 to about 700 mg carisoprodol, or a pharmaceutically acceptable salt or ester thereof, (b) a sweetener, (c) a flavoring agent, (d) a cyclodextrin, and (e) one or more additional excipients. The pharmaceutical composition can further comprise about 10% to about 50%, about 20% to about 40%, about 15% to about 35%, by weight of pharmaceutically acceptable excipients or carriers. In some embodiments, the chewable tablet further comprises an one or more additional active agents in an amount of from about 0.01 to about 0.25 parts, from about 0.01 to about 0.20 parts, or from about 0.01 to about 0.15 parts of the carisoprodol by weight. In some embodiments, the chewable tablet further comprises about 0.1% to about 2% cyclodextrin, and about 10% to about 50%, about 20% to about 40%, about 15% to about 35%, by weight of pharmaceutically acceptable excipients or carriers. Suitably, the compositions comprise carisoprodol comprising particles that are less than about 250 microns in size.

Orally Disintegrating Tablets

In another embodiment, the present invention provides orally disintegrating/or dispersible tablets, such as those disclosed in U.S. Pat. No. 6,723,348, the disclosure of which is incorporated herein by reference in its entirety for all purposes. The orally disintegrating/orodispersible tablets suitably disintegrate in the buccal cavity upon contact with saliva forming an easy-to-swallow suspension. Such tablets comprise (or consist essentially of) carisoprodol, and optionally, one or more one or more additional active agents (such as those described herein), in the form of coated granules, and a mixture of excipients comprising at least one disintegrating agent, a soluble diluent agent, a lubricant and optionally a swelling agent, an antistatic (fluid flow) agent, a permeabilising agent, taste-masking agents/sweeteners, flavoring agents and colors. In certain such embodiments, the disintegrating/orodispersible tablets comprise the taste-masking agent sucralose. The amounts of carisoprodol, other optional active agents, and sweetening agents (e.g., sucralose) in the orally disintegrating tablet formulations of the present invention are readily determinable by those of ordinary skill in the art, and include those amounts and combinations described herein. For example, the orally disintegrating tablet formulations of the present invention comprise about 10% to about 90%, or about 20% to about 80%, or about 30% to about 70%, or about 40% to about 60% carisoprodol, optionally about 0.01% to about 90%, or about 1% to about 70%, or about 10% to about 50%, or about 20% to about 30% other active agent(s) (or more as required), and about 0.05% to about 0.15% sucralose.

In suitable embodiments, the particles/granules of carisoprodol (and any other optional active agents) have a particle size such that about 100% of the particles have an average size of less than about 50 micrometers. In suitable such embodiments, carisoprodol (and any other optional active agents) are present as coated granules.

In one embodiment, the disintegrating tablets according to the invention comprise coated granules of carisoprodol (and optionally, one or more one or more additional active agents) or one of its pharmaceutically acceptable salts, a taste-masking agent such as sucralose, and a mixture of excipients, the ratio of the mixture of excipients to the coated granules suitably is about 0.4:1 to about 9:1, more suitable about 1.5:1 to about 5:1, or about 2 to 3 parts by weight, the mixture of excipients suitably comprising: at least one disintegrating agent, a soluble diluent agent, a lubricant, and optionally a permeabilising agent, a swelling agent, an antistatic agent, flavoring agents and one or more coloring agents.

In suitable embodiments, the disintegrating agent is selected from the group consisting of croscarmellose, available as e.g. Ac-di-Sol™, crospovidone available as e.g. Kollidon CL™, sodium starch glycolate and mixtures thereof.

According to one embodiment of the invention, the soluble diluent is a polyol having less than 13 carbon atoms and being either in the form of a directly compressible product with an average particle size of about 50 to 500 micrometers, or in the form of a powder with an average particle size of less than about 100 micrometers, this polyol suitably being selected from the group consisting of mannitol, xylitol, sorbitol and maltitol. The proportion of disintegrating agent suitably is from about 3 to about 15% by weight, e.g., about 5 to about 15% by weight, and in the case of a mixture, each disintegrating agent being present between about 1 and about 10% by weight, e.g., about 5 to about 10% by weight, and the proportion of soluble diluent agent being about 20 to about 80% by weight, e.g., about 30 to about 60% by weight, based in each case on the weight of the tablet.

Suitable lubricants for use in the disintegrating tablets include, but are not limited to, magnesium stearate, stearic acid, sodium stearyl fumarate, micronised polyoxyethyleneglycol (micronised Macrogol 6000), leukine, sodium benzoate and mixtures thereof. The amount of lubricant generally is from about 0 to about 3%, e.g., from about 1 to about 2% by weight, based on the weight of the tablet. The lubricant can be dispersed within the mixture of excipients, or according to one embodiment, sprayed over the outer surface of the tablet. Thus, according to one embodiment of the disintegrating tablets of the invention, the lubricant is in powder form and is, at least in part, disposed on the surface of the tablets.

The permeabilising agent allows the creation of a hydrophilic network which facilitates the penetration of saliva and hence assists the disintegration of the tablet. Suitable permeabilising agent include, but are not limited to, silica with a high affinity for aqueous solvents, such as colloidal silica (Aerosil™), precipitated silica (Syloid™ FP 244), maltodextrins, β-cyclodextrins and mixtures thereof. The amount of permeabilising agent suitably is between about 0 and about 5%, e.g., from about 0.5 to about 2% by weight, based on the weight of the tablet.

A swelling agent can be incorporated in the mixture of excipients. Suitable swelling agents include, but are not limited to, starch, modified starch, croscarmellose, Ac-DiSol or microcrystalline cellulose.

An antistatic agent can also be incorporated as a flow aid. Suitable antistatic agents include, but are not limited to, micronised or non-micronised talc, fumed silica (Aerosil™ R972), colloidal silica (Aerosil™ 200), precipitated silica (Syloid™ FP 244), and mixtures thereof.

According to one such embodiment of the invention, the granules of carisoprodol or one of its pharmaceutically acceptable salts (and optionally, one or more additional active agents such as those described herein) are characterized in that the granules are coated and comprise microcrystals of carisoprodol or one of its pharmaceutically acceptable salts, sucralose, at least one binder, and optionally a diluent agent, an antistatic agent, and a coloring agent. Furthermore, the granulation excipients can also include disintegrating agents and/or surfactants.

Suitable binders include, but are not limited to, cellulosic polymers, such as ethylcellulose, hydroxypropylcellulose and hydroxypropylmethyl cellulose, acrylic polymers, such as insoluble acrylate ammoniomethacrylate copolymer, polyacrylate or polymethacrylic copolymer, povidones, copovidones, polyvinylalcohols, alginic acid, sodium alginate, starch, pregelatinized starch, sucrose and its derivatives, guar gum, polyethylene glycol, for example an acrylic polymer, such as Eudragit™ E100, and mixtures thereof.

Optionally, in order to enhance the granulation of the carisoprodol (and one or more one or more additional active agents) or one of its pharmaceutically acceptable salts, a diluent agent can be used. Suitable diluent agents include, but are not limited to, microcrystalline cellulose, sucrose, dicalcium phosphate, starches, lactose and polyols of less than 13 carbon atoms, such as mannitol, xylitol, sorbitol, maltitol, pharmaceutically acceptable amino acids, such as glycin, and their mixtures.

In one embodiment, a granule of carisoprodol or one of its pharmaceutically acceptable salts (as well as any one or more additional active agents, such as those described herein), can be in the form of a core of granulated microcrystals of carisoprodol, coated with at least one layer comprising carisoprodol. Such a coated core is characterized in that the core and the layer comprise each from 70% to 95%, preferably 80% to 95% by weight of carisoprodol, or one of the pharmaceutically acceptable salts thereof, the balance to 100% being formed with at least one binder and optionally sucralose, and that the coated core is suitably a sphere. See e.g., French patent application FR 00 14803, the disclosure of which is incorporated by reference herein.

In one embodiment of the invention, the granules can comprise (or consist essentially of): from about 10% to about 95%, e.g., from about 50% to about 70% of carisoprodol or a pharmaceutically acceptable salt thereof and optionally one or more one or more additional active agents, such as those described herein, at most about 5 to about 10% by weight of the binder, relative to the weight of carisoprodol, or one of the pharmaceutically acceptable salts thereof, at most about 5%, suitably about 2% by weight of the antistatic agent, relative to the weight of the granules, suitably about 0.05% to about 5% sucralose and optionally a diluent agent for the balance to 100%.

The granules can also be coated with a coating composition comprising at least one coating polymer selected from the group consisting of cellulosic polymers, acrylic polymers and their mixtures. Among the cellulosic polymers, ethylcellulose, hydroxypropylcellulose (HPC) and hydroxypropylmethylcellulose (HPMC), can be used. Among the acrylic polymers, insoluble acrylate ammonio-methacrylate copolymer (Eudragit™ RL100 or RS100 or Eudragit™ RL30D or RS30D), polyacrylate (Eudragit™ NE30D), or methacrylic copolymers (e.g., Eudragit™ L100-55 Eudragit™ L30D, Eudragit™ E100 and Eudragit™ EPO) can be used, alone, in combination, or in admixture with pH-dependent polymers. Eudragit™ E100 or a mixture of Eudragit™ EPO and Eudragit™ NE30D are suitably used. In one embodiment, the binder and the coating polymer are the same polymer.

Optionally, permeabilising agents, plasticizers, soluble agents, disintegrating agents and surfactants, can be added as coating additives. Suitable plasticizers include, but are not limited to, triacetine, triethylacetate, triethylcitrate (Eudraflex™), ethylphthalate, or mixtures thereof. The plasticizer is used in proportions of at most about 30%, preferably 10% by weight of the coating polymers. Suitable soluble agents include polyols having less than 13 carbon atoms. Surfactants may be an anionic, nonionic, cationic, zwitterionic or amphoteric surfactant. Suitable disintegrating agents include, but are not limited to, croscarmellose, available as e.g. Ac-di-Sol™, crospovidone available as e.g. Kollidon CL™, and mixtures thereof.

Suitably, the coated granules according to the present invention have a particle size distribution between about 150 micrometers and about 500 micrometers, more suitably between about 150 micrometers and about 425 micrometers, such that at least 50%, more suitably at least 70% of the granules have a particle size ranging between about 150 and about 425 micrometers, and less than 15% of the granules have a particle size less than about 150 micrometers.

In one embodiment, the coated granules according to the invention comprise: from about 10% to about 95%, preferably about 40 to about 75% of granules of carisoprodol or one of its pharmaceutically acceptable salts, suitably carisoprodol and optionally one or more optional one or more additional active agents, such as those disclosed herein, sucralose from about 0.05% to about 5%, from about 5 to about 90%, suitably about 10 to about 70% and even more suitably from about 25 to about 55% of a coating polymer, such as Eudragit™ E100, the percentages being expressed by weight relative to the weight of the granules of carisoprodol, or one of its pharmaceutically acceptable salts, from about 0 to about 10% of a permeabilising agent, such as colloidal silica, the percentages being expressed by weight relative to the weight of the coating polymer.

Effervescent Formulations

In another embodiment, the present invention provides a solid, effervescent, rapidly dissolving dosage form of carisoprodol for oral administration, such as disclosed in U.S. Pat. No. 6,245,353, the disclosure of which is incorporated by reference herein in its entirety. In such an embodiment, the effervescent formulation comprise (or consist essentially of) (a) carisoprodol or a pharmaceutically acceptable salt thereof, and optionally one or more one or more additional active such as those disclosed herein, (b) an effervescent base comprising at least one of (i) at least one of (1) an organic edible acid and (2) a salt thereof, (ii) at least one of an alkali metal and an alkaline earth metal carbonate and bicarbonate, and (c) optionally a pharmaceutically acceptable auxiliary agent. In certain suitable embodiments, the effervescent formulations further comprise one or more taste-masking agents, such as sucralose, and/or other taste-masking agents described herein. The amounts of carisoprodol, other optional active agents (e.g., a non-aspirin NSAID, one or more muscle relaxing compounds, one or more anxiolytic compounds, one or more narcotic analgesics, one or more non-narcotic analgesics, one or more anticonvulsants, one or more antipsychotics, one or more antidepressants and combinations thereof), and sweetening agents (e.g., sucralose) in the effervescent formulations of the present invention are readily determinable by those of ordinary skill in the art, and include those amounts and combinations described herein. For example, the effervescent formulations of the present invention comprise about 10% to about 90%, or about 20% to about 80%, or about 30% to about 70%, or about 40% to about 60% carisoprodol, optionally about 0.01% to about 90%, or about 1% to about 70%, or about 10% to about 50%, or about 20% to about 30% other active agent(s) (or more as required), and about 0.05% to about 0.15% sucralose.

A solution or suspension of carisoprodol or salt thereof is formed by adding water to the soluble or dispersible effervescent tablets or soluble granules, with evolution of $CO_2$ gas. The resulting effervescent solution or suspension can be ingested very easily, even by patients who have difficulties swallowing. The rapidly disintegrating tablet can also be administered so that it directly disintegrates in the mouth. A rapid release of the active agent is of particular importance here, to ensure a rapid onset of action.

Effervescent agents capable of releasing $CO_2$, which can be used in the present invention, include alkali metal carbonates or alkali metal bicarbonates, such as sodium carbonate or sodium bicarbonate. Agents for inducing $CO_2$ release which are suitably employed are edible organic acids, or their acidic salts, which are present in solid form and which can be formulated with the carisoprodol active agent and the other auxiliary agents (as well as any other active agents) to provide granules or tablets, without premature evolution of $CO_2$. Edible organic acids which can be so used include for example, tartaric acid, malic acid, fumaric acid, adipic acid, succinic acid, ascorbic acid, maleic acid or citric acid. Pharmaceutically acceptable acidic salts include, for example, salts of polybasic acids which are present in solid form and in which at least one acid function is still present, such as sodium dihydrogen or disodium hydrogen phosphate or monosodium or disodium citrate.

In one embodiment, the present invention provides effervescent carisoprodol formulations including the formulations and compositions described herein, having an effervescent base comprising (a) a mixture of calcium carbonate with an organic edible acid; (b) a mixture of calcium carbonate, sodium carbonate, sodium bicarbonate and an organic edible acid; or (c) a mixture of sodium bicarbonates, sodium carbonate and an organic edible acid.

The soluble or dispersible effervescent carisoprodol tablets or the soluble granules suitably comprise (or consisting essentially of) from about 100 mg to about 700 mg carisoprodol (or salt thereof) and from about 50 mg to about 5000 mg, suitably from about 500 mg to about 3000 mg of an effervescent base, optionally, along with other active agents (such as those described herein) and excipients, including taste-masking agents such as sucralose, suitably at about 0.05% to about 5%.

The effervescent base suitably comprises from about 100 mg to about 500 mg calcium ions as, for example, calcium carbonate, and from about 20 mg to about 1500 mg citric acid and/or its salts. In another embodiment, the effervescent base comprises from about 50 mg to about 2000 mg sodium bicarbonate, from about 20 mg to about 200 mg of sodium carbonate and from about 20 mg to about 1500 mg citric acid and/or from about 20 mg to about 500 mg tartaric acid.

An additional suitable composition of the effervescent base comprises from about 50 mg to about 500 mg sodium bicarbonate, from about 20 mg to about 100 mg sodium carbonate, and from about 50 mg to about 750 mg calcium carbonate and from about 100 mg to about 1500 mg of citric acid.

The soluble/dispersible tablets can be prepared by known processes for preparing effervescent bases, such as those disclosed in U.S. Pat. No. 6,245,353, the disclosure of which is incorporated herein by reference in its entirety.

Orally Dissolving/Consumable Films

Another embodiment of the present invention is directed to a physiologically acceptable film that is particularly well-adapted to dissolve in the oral cavity of a warm-blooded animal including humans, and adhere to the mucosa of the oral cavity, to allow delivery of carisoprodol or a salt thereof, and optionally one or more one or more additional active agents such as those described herein. Such physiologically acceptable films suitable for use in accordance with this aspect of the present invention are disclosed in U.S. Patent Application No. 2004/0247648, the disclosure of which is incorporated herein by reference in its entirety.

In one such embodiment of the present invention, an orally dissolving/consumable film comprises a modified starch, carisoprodol or a salt thereof, and optionally, one or more one or more additional active agents such as those described herein, suitably, one or more taste-masking agents, such as sucralose, and optionally, at least one water soluble polymer. The amounts of carisoprodol, other optional active agents, and sweetening agents (e.g., sucralose) in the orally dissolving/consumable film formulations of the present invention are readily determinable by those of ordinary skill in the art, and include those amounts and combinations described herein. For example, the orally dissolving/consumable film formulations of the present invention comprise about 100 mg to about 700 mg carisoprodol, optionally about 0.5 mg to about 1000 mg other active agent(s), and about 0.05% to about 0.15% sucralose.

The consumable films of the present invention may comprise one or more of the following agents: water, antimicrobial agents, additional film forming agents or water soluble polymers, plasticizing agents, flavorings, sulfur precipitating agents, saliva stimulating agents, cooling agents, surfactants, stabilizing agents, emulsifying agents, thickening agents, binding agents, coloring agents, triglycerides, polyethylene oxides, propylene glycols, additional taste-masking agents or sweeteners, fragrances, preservatives and the like, as described in U.S. Pat. No. 6,596,298, the disclosure of which is incorporated by reference herein in its entirety.

In one such embodiment, the consumable films of the present invention include a modified starch. The modified starches used in accordance with the present invention can be prepared by mechanically, chemically or thermally modifying unmodified starches. For example, modified starches may be prepared by chemically treating starches to produce, for example, acid treatment starches, enzyme treatment starches, oxidized starches, cross-bonding starches, and other starch derivatives. Starches suitable for modification to produce modified starches may be obtained from natural products such as corn, potatoes, tapioca as well as genetically modified forms of the same such as high amylose and waxy corn as well as sorghum varieties.

Examples of modified starches for use in the practice of the present invention include, but are not limited to, modified corn starches, modified tapioca starches, acid and enzyme hydrolyzed corn and/or potato starches, hypochlorite-oxidized starches, acid-thinned starches, ethylated starches, cross-bonded starches, hydroxypropylated tapioca starches, hydroxypropylated corn starches, pregelatinized modified starches, and the like. Preferred modified starches are selected from pregelatinized modified corn starches and pregelatinized modified tapioca starches.

Representative examples of commercially available modified starches useful in the present invention include PURE-COTE™ modified starches such as PURE-COTE™ B793 (a pregelatinized modified corn starch) and PURE-COTE™ B795 (a pregelatinized modified corn starch), for example, available from Grain Processing Corporation, 1600 Oregon Street, Muscatine, Iowa 52761-1494 USA.

In one such embodiment of the present invention, the modified starch is present in amounts ranging from about 1% to about 90% by weight, in another embodiment about 10% to about 90% by weight, and in yet another embodiment from about 35% to about 80% by weight of the film.

Modified starch may be included in the film alone or optionally in combination with an additional water soluble film forming polymers such as those selected from, for example, pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymers, carboxyvinyl polymers, amylose, high amylose starch, hydroxypropylated high amylose starch, pectin, dextrin, chitin, chitosan, levan, elsinan, collagen, gelatin, zein, gluten, soy protein isolate, whey protein isolate, casein and combinations thereof. A preferred water soluble polymer is pullulan. The amount of the water soluble polymer typically is up to about 99% by weight, suitably up to about 80% by weight, more suitably up to about 50% by weight, and most suitably up to about 40% by weight of the film.

Microcapsules ("Sprinkle") Formulations

A population of patients experience physical or psychological difficulty swallowing either whole tablets or capsules, preferring instead liquid suspensions, chewable tablets, or microcapsules. However, certain active agents are particularly bitter or unpalatable and therefore unsuitable for administration in a physical form in which the active agent is more likely to be tasted, such as a liquid suspension or chewable tablet.

Microcapsules, on the other hand, typically have a size and shape that is acceptable to most patients for swallowing in whole form and can be prepared with a taste-masking layer. Microcapsules are usually spherically shaped and have a size of about a millimeter or smaller. A gelatin capsule is often used to encapsulate a plurality of microcapsules and is formulated to contain a predetermined amount of the required active agent. If the patient has difficulty swallowing the gelatin capsule in whole form, some capsules are designed to be opened so that the microcapsules can be "sprinkled" into the mouth and swallowed with water. Alternatively, the microcapsules can be sprinkled onto a spoonful serving of a food such as apple sauce or yoghurt and can be swallowed without chewing.

Various pharmaceutical compositions containing coatings or layers have been proposed. See, for example, U.S. Pat. Nos. 4,800,087; 4,874,613; 5,026,560; 5,891,474; 6,207,197; and 6,696,091.

Release of the active agent from a taste-masked microcapsule is usually designed to occur in the patient's stomach or intestines. Microcapsules can be formulated with any one of a number of release profiles, such as delayed release, delayed-extended release, extended release, immediate release, pulsed release and sustained release.

The pharmaceutical compositions of the present invention can be formulated in the form of such microcapsules and can then be sprinkled into the mouth or on top of food to facilitate swallowing of the pharmaceutical composition.

Some embodiments of the present invention provides a pharmaceutical composition in the form of microcapsules comprising (a) core particles containing carisoprodol, wherein the core particles have an initial particle size between about 100 micrometers and 500 micrometers; and (b) a taste mask coating, wherein the taste mask coating comprises between about 7% by weight and about 15% by weight of the carisoprodol, and wherein the coated particles of the pharmaceutical composition have a final particle size of about 0.100 mm to about 1.00 mm.

In some embodiments of the present invention, the microcapsules can comprise from about 1% to about 90%, about 5% to about 80%, about 10% to about 70%, or about 15% to about 60% by weight of carisoprodol, or a pharmaceutically acceptable salt or ester thereof. In some embodiments, the pharmaceutical composition further comprises an one or more additional active agents in an amount of from about 0.01 to about 0.25 parts, from about 0.01 to about 0.20 parts, or from about 0.01 to about 0.15 parts of the carisoprodol by weight. The pharmaceutical composition can further comprise about 10% to about 90%, about 20% to about 80%, about 30% to about 70%, or about 40% to about 60% by weight of other pharmaceutically acceptable excipients or carriers.

Controlled and/or Extended Release Formulations

Extended release drug delivery systems are designed in an attempt to satisfy the spatial placement and temporal delivery of a drug. Extended release drug delivery systems include any drug delivery system that achieves slow release of a drug over an extended period of time. If these extended release drug delivery systems can provide some control of drug release in the body, whether this be of a temporal or spatial nature, or both, or in other words, the system is successful at maintaining drug levels in the target tissue or cells, it is considered to be a controlled release drug delivery system.

In another embodiment, the present invention provides extended release carisoprodol compositions. Methods for preparing extended release tablets, capsules, caplets, pellets and the like, as well as excipients for use in the extended release formulations of the present invention, are well known in the art, and can be found, for example, throughout the detailed description section and the Examples of U.S. Pat. No. 5,271,946, the disclosure of which is incorporated herein by reference in its entirety for all purposes.

In some embodiments of the present invention, the extended release or controlled release compositions of the present invention utilizes a specific particle size of carisoprodol. The incorporation of a specific particle size of carisoprodol into the composition contributes to an advantageous dissolution profile and acts as a deterrent to the misuse of the carisoprodol composition.

In some embodiments of the present invention, the extended release and/or controlled release compositions provided by the present invention suitably comprise from about 200 mg to 1000 mg, about 300 to about 900 mg, about 400 mg to about 800 mg, or about 500 mg to about 700 mg, of carisoprodol, or a pharmaceutically acceptable derivative, salt or ester thereof, as the active agent. For example, the extended release and/or controlled release compositions can comprise about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg of carisoprodol, or a pharmaceutically acceptable derivative, salt or ester thereof. Suitably, the controlled release formulations comprise carisoprodol that has a particle size such that greater than about 30% of the particles are about 150 microns or greater. More suitably, the carisoprodol has a particle size such that greater than about 40% of the particles are about 250 microns or greater.

The extended release or controlled release pharmaceutical compositions can comprise from about 50% to about 90%, or about 60% to about 80%, by weight of carisoprodol, or a pharmaceutically acceptable salt or ester thereof.

In some embodiments, the pharmaceutical composition further comprises one or more additional active agents in an amount of from about 0.01 to about 0.25 parts, from about 0.01 to about 0.2 parts, or from about 0.01 to about 0.15 parts, of the carisoprodol by weight. The pharmaceutical composition can further comprise about 10% to about 90%, about 20% to about 80%, about 30% to about 70%, or about 40% to about 60% by weight of pharmaceutically acceptable excipients or carriers. As discussed in U.S. Pat. No. 5,271,946, the extended release formulations of the present invention can be obtained as follows:

1. Through binding of carisoprodol or a pharmaceutically acceptable salt thereof, and optionally one or more one or more additional active agents such as those described herein, to physiologically acceptable ion exchanger resins. The following may, for example, be used as such cation exchangers: acrylic and methacrylic resins with exchangeable protons, acid groups: $COO^-$ e.g. Amberlite™ IRP-64 Polystyrene resins with exchangeable $Na^+$, acid groups: $SO_3^-$, e.g. Amberlite™ IRP-69.

2. Coating of active agent particles, granulate or pellet grains or carisoprodol-containing tablets with coatings of the following substances, or mixtures of the following substances: hydroxypropylmethyl cellulose phthalate- or acetate succinate; cellulose-, starch-, as well as polyvinyl acetate phthalate; carboxymethyl cellulose; hypromellose; carbopol starch acetate; cellulose acetate; polyvinyl acetate; methylcellulose phthalate, methylcellulose succinate, methyl cellulose phthalate succinate as well as methyl cellulose phthalic acid half ester; zein; ethyl cellulose as well as ethyl cellulose succinate; shellac; gluten; ethylcarboxyethyl cellulose; ethacrylate-maleic acid anhydride copolymer; maleic acid anhydride vinyl methyl ether copolymer; sterol maleic acid copolymerizate; 2-ethylhexylacrylate maleic acid anhydride; crotonic acid vinyl acetate copolymer; glutaminic acid/ glutaminic acid ester copolymer; carboxymethylethyl cellulose glycerin mono-octanoate; cellulose acetate succinate; polyarginin; fats, oils, waxes, fatty alcohols; anionic polymerizates of methacrylic acid and methacrylic acid esters (Eudragit™ L, Eudragit™ S); copolymerizates of acrylic and methacrylic acid esters with a low ammonium group (Eudragit™ RS) content, as well as copolymers of acrylic and methacrylic acid esters and trimethyl ammonium methacrylate (Eudragit™ RL), copolymerizates of acrylic acid ethyl- and methacrylic acid methyl esters 70:30 (Eudragit™ NE 30 D), copolymerizates of acrylic acid, methacrylic acid as well as their esters (ratio of the free carboxyl groups to the ester groups for example 1:1) (Eudragit™ L 30 D).

Such extended release formulations may also contain conventional softeners or plasticizers (e.g. dibutyl sebacate, citric and tartaric acid esters, glycerin and glycerin esters, phthalic acid esters and similar substances). It also is possible to add water-soluble substances such as polyethylene glycols, polyvinylpyrrolidone, copolymerizates of polyvinylpyrrolidone and polyvinyl acetate, hydroxypropyl cellulose, hydroxypropylmethyl cellulose. The addition of solids such as talcum and/or magnesium stearate to the coating is also possible.

Organic acids (such as for example citric acid, tartaric acid, maleic, fumaric, ascorbic acid) may also be incorporated into the pellet grains, granulate grains or tablets.

3. Coating of pressed disks, tablets, granulates containing the carisoprodol or salt thereof, and optionally one or more one or more additional active agents such as those described herein, and one or more osmotically active substances, (e.g. mannitol, sorbitol and the like) with a semi-permeable membrane, e.g. of 70 to 90 weight % of cellulose acetate and hydroxypropylmethyl cellulose or hypromellose (30 to 10 weight %).

Other osmotically active substances that can be used include organic and inorganic compounds or soluble substances which generate an osmotic pressure gradient as compared to the outer liquid via the semi-permeable wall. Osmotically active agents or osmotically active compounds include magnesium sulfate, magnesium chloride, sodium chloride, lithium chloride, potassium sulfate, potassium hydrogen phosphate, urea, saccharose and the like. Other osmotically active agents are disclosed in U.S. Pat. Nos. 3,854,770, 4,077,407 and 4,235,236, the disclosures of each of which are incorporated herein by reference in their entireties.

Semi-permeable materials which can be used as polymers for osmosis and reverse osmosis are, for example: cellulose acylate, cellulose diacylate, cellulose triacylate, cellulose acetate, cellulose diacetate, cellulose triacetate, β-glucan acetate, acetaldehyde dimethyl acetate, cellulose acetate ethyl carbamate, polyamide, polyurethane, sulphonated polystyrene, cellulose acetate phthalate, cellulose acetate methyl carbamate, cellulose acetate succinate, cellulose acetate dimethylamino acetate, cellulose acetate chloracetate, cellulose dipalmitate, cellulose dioctanoate, cellulose dicaprylate, cellulose dipentanate, cellulose acetate valerate, cellulose acetate-p-toluene sulphonate, cellulose acetate butyrate, ethyl cellulose, selectively permeable polymers which are formed by joint precipitation of a polycation and a polyanion as disclosed in U.S. Pat. Nos. 3,173,876, 3,276,586, 3,541, 005, 3,541,006 and 3,546,142, the disclosures of which are incorporated by reference herein in their entireties. Coatings of this type in semi-permeable membranes may for example also be effected according to U.S. Pat. Nos. 4,455,143 and 4,449,983, the disclosures of which are incorporated by reference herein.

The proportion of osmotically active substance can be from about 10 to about 800 parts by weight, suitably about 20 to about 600, and more suitably about 50 to about 400 parts by weight, based on 1 part by weight of carisoprodol. The amount of coating substances applied is such that the semi-permeable membrane is about 50 to about 500 micrometers, suitably about 100 to about 300 micrometers thick.

4. Embedding of or binding carisoprodol (or salt thereof) and/or any other optional one or more additional active agents(s) to the following substances or mixtures of these substances:

Digestible fats, such as triglycerides of saturated fatty acids, $C_8H_{16}O_2$ to $C_{18}H_{36}O_2$, and mixtures thereof, peanut oil and hydrated peanut oil, castor oil and hydrated castor oil, olive oil, sesame oil, cottonseed oil and hydrogenated cottonseed oil, corn oil, wheat germ oil, sunflower seed oil, cod liver oil, mixtures of mono-, di- and triesters of palmitic and stearic acid with glycerine, glycerine trioleate, diglycol stearate, stearic acid.

Indigestible fats or fat-like substances, for example esters of aliphatic saturated or unsaturated fatty acids (2 to 22 carbon atoms, in particular 10 to 18 carbon atoms) with monovalent aliphatic alcohols (1 to 20 carbon atoms), carnauba wax, beeswax, fatty alcohols (straight chain or branched) of chain length $C_8H_{17}OH$ to $C_{30}H_{61}OH$, in particular $C_{12}H_{25}OH$ to $C_{24}H_{49}OH$.

Polymers such as polyvinyl alcohol, polyvinyl chloride, polyacrylic acid (Carbopol™); anionic polymerizates of methacrylic acid and methacrylic acid esters (Eudragit™ L, Eudragit™ S), acrylic and methacrylic acid ester copolymerizates with trimethyl ammonium methacrylate (Eudragit™ RL, Eudragit™ RS).

Copolymerizates of ethyl acrylates and methyl methacrylates (Eudragit™ NE 30 D), as well as of acrylic acid, methacrylic acid as well as esters thereof (ratio of free carboxyl groups to ester groups 1:1) (Eudragit™ L 30 D), polyethylene, polyglycolic acid, polyhydroxybutyric acid, polylactic acid, copolymers of lactic acid and glycolic acid (manufacturer: Boehringer Ingelheim), copolymers of lactic acid and ethylene oxide, copolymers of glycolic acid and ethylene oxide, copolymers of lactic acid and hydroxybutyric acid, hydroxypropylmethyl cellulose-phthalate or -acetate succinate; cellulose acetate phthalate, starch acetate phthalate as well as polyvinyl acetate phthalate; carboxymethyl cellulose; methylcellulose phthalate, -succinate, -phthalate succinate, methyl cellulose phthalic acid half ester; zein; ethyl cellulose; shellac, gluten; ethylcarboxyethyl cellulose; ethacrylate maleic acid anhydride copolymer; maleic acid anhydride vinyl methyl ether copolymer; styrene maleic acid copolymerizate; 2-ethylhexyl acrylate maleic acid anhydride; crotonic acid vinyl acetate copolymer; glutaminic acid/ glutaminic acid ester copolymer; carboxymethyl cellulose glycerine mono-octanoate; cellulose acetate succinate; polyarginine; cross-linked alginate; cross-linked gelatin.

Swelling agents such as methyl cellulose, hydroxypropyl cellulose, hydroxypropyl methyl cellulose (Pharmacoat, Methocel E (propylene glycol ether of methyl cellulose)), alginic acid and their salts (Na⁻, Ca⁻ salt, also mixtures of sodium alginate and calcium salts such as $CaHPO_4$), starch, carboxymethyl starch, carboxymethyl cellulose and their salts (e.g. Na⁻ salts), galacto mannan, gum arabic, karaya rubber, ghatti gum, agar-agar, carrageen, xanthan rubber, guar rubber and its derivatives, carob bean flour, propylene glycol alginate, pectin, tragacanth.

Suitable exemplary extended release components are:

a) Cation exchangers: Sodium poly(styrene, divinylbenzene)sulphonate (e.g. Amberlite™ IRP 69). Suitably 3 to 10 parts of Amberlite™ IRP 69 are for example used per 1 part of carisoprodol (base).

b) Coating substances: Hydroxypropylmethyl cellulose phthalate, suitably at 1.5 to 3 parts of hydroxypropyl methyl cellulose phthalate 55 are used per 1 part of carisoprodol. Ethyl cellulose, suitably 0.1 to 1 part of ethyl cellulose are used per 1 part of carisoprodol. Eudragit resins, for example Eudragit™ RS 0.01 to 0.1 part of Eudragit™ RS per 1 part of carisoprodol.

c) Semi-permeable layers with osmotically acting active substance containing core and outlet openings: Coating with 100 to 300 μm thick layer of 82% cellulose acetate and 18% hydroxypropyl methyl cellulose.

d) Embedding substances: Hydrocolloids e.g. hydroxypropyl methyl cellulose: 0.01 to 0.05 parts of hydrocolloid per 1 part of carisoprodol. Eudragit™ RS: 10 to 15 parts of Eudragit™ RS per 1 part of carisoprodol. Glycerineditripalmito stearate (e.g. Precirol Ato 5) 1 to 10 parts of Precirol Ato 5 per 1 part of carisoprodol.

In some embodiments of the present invention, the extended release or controlled release composition is in the form of a tablet comprising:

i) carisoprodol or both the carisoprodol and the one or more additional active agents; and ii) at least one functional ingredient which provides for extended release of the carisoprodol alone or both the carisoprodol and the one or more additional active agents for a period of up to about 12 hours or up to about 24 hours. In some embodiments, the pharmaceutical composition provides extended release of the carisoprodol, optionally with an one or more additional active agents, for about 24 hours. In some embodiments, the coating comprises a cellulose derivative, a methacrylic copolymer, or a resin, wherein the coating is present in an amount that is 1.5 to 3 parts of coating per 1 part of carisoprodol.

In some embodiments of the present invention, the extended release pharmaceutical composition is in the form of a tablet, wherein carisoprodol, or both carisoprodol and the additional active agents is bound to at least one cation exchanger and provides extended release of the carisoprodol or the one or more additional active agents, or both the carisoprodol and the additional active agent for a period greater than 12 hours.

In some embodiments, the extended release pharmaceutical composition of the present invention is in the form of a tablet, wherein carisoprodol or both carisoprodol and the one or more additional active agents are embedded in an embedding substance which provides extended release of the carisoprodol or both the carisoprodol and the additional active agent for a period 12 to 24 hours. In some embodiments, the pharmaceutical composition provides extended release of the carisoprodol for a period of about 12 to 24 hours and additionally provides immediate release of carisoprodol and any additional active agents. In some embodiments, the pharmaceutical composition comprises 2 to 10 parts of the embedding substance per 1 part of carisoprodol, wherein the embedding substance is a hydrocolloid.

The oral dosage forms according to the invention are suitable for twice-daily or, preferably, once-daily administration of the carisoprodol compositions. The oral controlled release formulation according to the invention may be presented, for example, as tablets, multiparticulates, such as granules, spheroids, pellets, mini-tablets or sachets, capsules, or in any other suitable dosage form incorporating such multiparticulates. If desired, capsules such as hard or soft gelatin capsules, can contain the multiparticulates. If desired, the multiparticulate oral dosage forms can comprise a blend of at least two populations of spheroids, pellets or mini-tablets having different controlled-release in vitro carisoprodol release profiles. If desired, one of the spheroid, pellet or mini-tablet populations can comprise immediate release carisoprodol multiparticulates, such as multiparticulates formed by conventional means. A second population of spheroids, pellets or mini-tablets comprise controlled release carisoprodol multiparticulates. Also, a population of spheroids, pellets or mini-tablets can comprise controlled release carisoprodol multiparticulates coated with a controlled release or an enteric film coat. Further, the multiparticulates of the invention can be compressed into tablets.

The active agents in the pharmaceutical compositions according to the invention can be incorporated in a controlled release matrix. This may be any matrix that affords controlled release of the active agents over at least a twelve hour period in vivo.

Suitable materials for inclusion in a controlled release matrix include hydrophilic or hydrophobic polymers, such as gums, cellulose ethers, acrylic resins and protein derived materials. Examples of hydrophilic polymers to be used in this invention include hydroxyalkylcellulose, such as hydroxypropylcellulose and hydroxypropylmethylcellulose; poly(ethylene)oxide; alkylcellulose such as ethylcellulose and methylcellulose; carboxymethylcellulose; hydrophilic cellulose derivatives; polyethylene glycol; polyvinylpyrrolidone; cellulose acetate; cellulose acetate butyrate; cellulose acetate phthalate; cellulose acetate trimellitate; polyvinylacetate phthalate; hydroxypropylmethylcellulose phthalate; and hydroxypropylmethylcellulose acetate succinate. Of these polymers, the cellulose ethers, especially hydroxyalkylcellulose, are preferred. Examples of hydrophobic polymers to be used in this invention include poly(alkyl methacrylate) and poly(vinyl acetate). Other suitable hydrophobic polymers include polymers or copolymers derived from acrylic or methacrylic acid esters, copolymers of acrylic and methacrylic acid esters, zein, and shellac. The formulation may conveniently contain about 1-50% by weight of one or more hydrophilic or hydrophobic polymers depending on their viscosity.

In some embodiments of the invention the extended release formulations utilize one or more grades of hydroxypropylmethyl cellulose having a final viscosity in the range of 50 cps to 150 cps.

The controlled release matrix may also contain other pharmaceutically acceptable agents, i.e., excipients, which are conventional in the pharmaceutical art such as diluents, lubricants, binders, granulating aids, colourants, flavourants, surfactants, pH adjusters, anti-adherents and glidants, e.g. dibutyl sebacate, ammonium hydroxide, oleic acid and colloidal silicon dioxide. Suitable diluents include pharmaceutically acceptable inert fillers such as microcrystalline cellulose, lactose, dibasic calcium phosphate, saccharides, and/or mixtures of any of the foregoing. The diluent is suitably a water soluble diluent. Examples of diluents include microcrystalline cellulose such as Avicel® PH112, Avicel® PH101 and Avicel® PH102; Silicified microcrystallinecellulose such as Prosolv, lactose such as lactose monohydrate, lactose anhydrous, and Lactose Fast-Flo®; dibasic calcium phosphate; mannitol; starch; sorbitol; sucrose; and glucose. The diluent is preferably used in an amount of from 5 to 30% by weight of dosage unit, preferably from 10 to 25% by weight of dosage unit, of the controlled release formulation.

Suitable lubricants, including agents that act on the flowability of the powder to be compressed are, for example, colloidal silicon dioxide such as Aerosil 200, talc, stearic acid, magnesium stearate, and calcium stearate, castor oil and hydrogenated castor oil, and/or polyethylene glycol.

Suitable binders include starch paste, for example, maize starch, wheat starch, rice starch, potato starch, gelatin, tragacanth, methyl cellulose, hydroxypropylmethylcellulose, sodium carboxymethylcellulose, and/or polyvinyl pyrrolidone, polyethylene glycols such as PEG 6000, cetostearyl alcohol, cetyl alcohol, polyoxyethylene alkyl ethers, polyoxyethylene castor oil derivatives, polyoxyethylene sorbitan fatty acid esters, polyoxyethylene stearates, poloxamers, and waxes. If desired, disintegrating agents can be added, such as, the above-mentioned starches and also carboxymethylstarch, cross-linked polyvinyl pyrrolidone, agar, or alginic acid or a salt thereof, such as, sodium alginate. Other suitable disintegrants include, but are not limited to, croscarmellose, crospovidone and sodium starch glycolate.

One useful form of unit dose form in accordance with the invention comprises a capsule filled with immediate and controlled release spheroids (pellets) as described above. Suitable capsules include push-fit capsules made of gelatin, as well as soft, sealed capsules made of gelatin and a plasticizer, such as, glycerol or sorbitol. The push-fit capsules can contain a plurality of the controlled release spheroids (pellets) according to the invention that may optionally be mixed with fillers such as lactose, binders such as starches, and/or lubricants such as talc or magnesium stearate and, optionally, stabilizers.

In further embodiments, the extended release formulation may contain corisoprodol at about 58.5% carisoprodol USP (intragranular) about 10-13% carisoprodol USP (extragranular), and about 5.75% ProSolv 90 HD, about 7-18% Methocel K100 Premium LV CR (Hypromellose 2208, USP), about 4.0% sodium starch glycolate, NF, about 0.5% colloidal silicon dioxide, NF and about 1-2% magnesium stearate, NF, and QS calcium phosphate dibasic, by mass of the tablet. (714.3-1000 mg total)

In a further embodiment, the extended release formulation may contain about 58.5% carisoprodol USP (intragranular), about 5% Hypromellose E5, about 10-13% carisoprodol USP (extragranular), about 5-11% Methocel K100 Premium LV CR (Hypromellose 2208, USP), about 5% ProSolv 90 HD, about 0.5% colloidal silicon dioxide and about 1-3% magnesium stearate, NF, by mass of the tablet. (714.3-1000 mg)

In a still further environment, the extended release formulation may contain about 350 to 900 mg of carisoprodol, USP; about 10 to 150 mg diclofenac potassium; about 15 to 175 mg of ProSolv 90 HD; about 15 to 160 mg of Methocel K100

Premium LV CR (Hypromellose 2208, USP), about 25 to 250 mg of calcium phosphate dibasic, USP; about 5 to 120 mg of sodium starch glycolate, NF; about 0.10 to 20 mg of colloidal silicon dioxide, NF; and about 2 to 30 mg of magnesium stearate, NF per mg tablet. (350 to 1500 total weight)

Controlled or Delayed Onset and Extended Release Formulations

Some patients may require that the dose of a drug be administered in a time varying pattern of delivery such as a drug free interval followed by an extended release of the drug for an extended period of time. For example, a patient may be prone to back muscle spasms during the early morning hours (for example, muscle spasms associated with the sudden movement of getting out of bed). This muscle pain, which occurs at waking, requires a dosage form that is administered upon retiring which dosage form delivers its drug before waking but after a drug free interval during sleep. This time varying pattern or controlled onset of drug delivery provides the required therapy at the appropriate time, thereby substantially lessening the instance of waking muscle pains.

U.S. Pat. No. 6,500,459 (the '459 patent) discloses a pharmaceutical composition for controlled onset and extended release of an active agent, the composition comprising: (i) a core comprising: (a) an active agent; (b) a hydrophilic carrier; (c) a hydrodynamic diffusion enhancer; and optionally (d) conventional pharmaceutically acceptable excipients selected from the group consisting of binders, fillers and lubricants and combinations thereof; and (ii) a functional coating membrane surrounding the core.

As disclosed in the '459 patent, the hydrophilic carrier can be one or more hydrophilic polymeric excipients in any desired ratio to provide a desired release profile of the active agent from the pharmaceutical composition. Preferably, the hydrophilic carrier is a homopolysaccharide or a heteropolysaccharide, preferably selected from the group consisting of xanthan gum, locust bean gum, propylene glycol ester, galactomannan, glucomannan, guar gum, gum acacia, gum tragacanth, alkali metal carageenates, alginates, cellulose alkyl carboxylates, carboxymethyl cellulose, carboxyethyl cellulose, alkali metal salts of cellulose alkyl carboxylates, sodium carboxymethyl cellulose, carboxypolymethylene, hydroxypropyl methylcelluloses, hydroxypropyl cellulose, hydroxyethyl cellulose, hydroxyethyl methyl cellulose, polyethylene glycols and polyethylene oxides, gellan gum, alginate salts, natural polysaccharides, gum arabica, etc. and combinations thereof. Some examples of polyethylene glycols and polyethylene oxides commercially available are those under the tradename Polyox® (Union Carbide, Danbury, Conn.). Any polymeric material that can hydrate and gel in the presence of water would be a suitable hydrophilic carrier for the pharmaceutical compositions of the present invention.

The '459 patent further discloses that the hydrodynamic diffusion enhancer is a substance which has the inherent capability of drawing water towards it, thereby increasing the rate at which water diffuses through a membrane, then absorbs this water, and swells and increases its volume and creates an internal hydrodynamic pressure. Preferably, the hydrodynamic diffusion enhancer is selected from the group consisting of gellan gum, starches, clays, celluloses, cellulose derivatives, alginates, crospovidone (Polyplasdone® and Polyplasdone® XL (ISP, Wayne, N.J.)), croscarmellose sodium (Ac-Di-Sol®, FMC Corp., Philadelphia, Pa.), sodium starch glycolate (Explotab®, Penwest, Patterson, N.Y.) and combinations thereof. Any excipient which has the inherent capability of drawing water towards it, thereby increasing the rate at which water diffuses through a membrane, then absorbs this water, and swells and increases its volume and creates an internal hydrodynamic pressure would be capable of functioning as a hydrodynamic diffusion enhancer and thus would be a suitable hydrodynamic diffusion enhancer for the pharmaceutical compositions of the present invention.

The '459 patent also discloses that the optional seal coating membrane, which is also typically known as a film coat, functions to seal all surface pores and to provide a uniform surface for the next coating step. The optional seal coating membrane is obtained by preferably spray coating seal coating dispersions onto the surface of uncoated cores using appropriate coating equipment. Usually these dispersions contain low viscosity hydrophilic polymers such as hydroxypropyl methylcellulose and hydroxypropyl cellulose, and plasticizers such as polyethylene glycol 400. These dispersions are commercially available as Opadry® Clear and Opadry® both from Colorcon, West Point, Pa. Similar seal coating dispersions are also available from other suppliers. The seal coating membrane is applied to the surface of an uncoated core to smooth out the surface of the core.

The functional coating membrane can be applied on top of the core or on top of the optional seal coating membrane. As disclosed in the '459 patent, the functional coating membrane can be an aqueous polymeric dispersion comprising dispersed plasticizers, film extenders and diffusion enhancers. Preferably, the functional coating membrane comprises ethylcellulose as an aqueous dispersion, preferably with appropriate coating agents dispersed therein.

The '459 patent further discloses that the optional top coating membrane allows the functional coating membrane to be coalesced. The optional top coating membrane is obtained by preferably spraying top coating dispersions onto the surface of the functional coating membrane. These top coating dispersions are commercially available as Opadry® white or Opadry® red, etc., named after the colorant present in the dispersion. Other equivalent brands of functional coating dispersions commercially available in the market are also suitable It is well known in the prior art to provide dosage forms that deliver their contents at a desired rate after a predetermined time delay. For example, the '459 discloses that there are two such controlled onset and extended release drug delivery systems currently on the market namely, Verelan® PM by Schwarz Pharma and Covera-HS™ by G. D. Searle & Co. Verelan® PM is a verapamil hydrochloride capsule formulation utilizing the proprietary CODAS™ (Chronotherapeutic Oral Drug Absorption System) technology, developed by Elan Corporation PLC and which technology is based on U.S. Pat. No. 4,863,742. U.S. Pat. No. 4,863,742 relates to a controlled absorption verapamil containing pellet formulation for oral administration comprising: (i) a core of (a) a powder mixture containing verapamil or a salt thereof and an organic acid, and (b) a polymeric material containing a major proportion of a water soluble polymer and a minor proportion of a water insoluble polymer, the core comprising layers of the powder mixture and the polymeric material superimposed one upon the other; and (ii) a multi-layer membrane surrounding the core and containing a major proportion of a film-forming, water insoluble polymer and a minor proportion of a film forming water soluble polymer; the release of the verapamil from the pellet being substantially independent of pH and at a rate allowing controlled absorption thereof over a 24 hour period following oral administration.

In accordance with examples from the '459 patent, the present invention provides a pharmaceutical composition for immediate release and extended release of carisoprodol, the composition comprising:

i) a core comprising:

(a) carisoprodol or a pharmaceutically acceptable derivative, salt or ester thereof;

(b) a hydrophilic carrier;

(c) a hydrodynamic diffusion enhancer; and optionally (d) conventional pharmaceutically acceptable excipients selected from the group consisting of binders, fillers and lubricants and combinations thereof; and (ii) a functional coating membrane surrounding the core, and optionally (iii) a seal coating membrane between the core and the functional coating membrane, and optionally (iv) a top coating membrane surrounding the functional coating membrane; wherein the composition provides an extended release of the carisoprodol from the composition for about 6 to about 24 hours. In some embodiments, the controlled onset and extended release pharmaceutical compositions of the present invention comprises a nanoparticle-based delivery system with embedded carisoprodol or a pharmaceutically acceptable derivative, salt or ester thereof. Such nanoparticle-based delivery systems are well know to those of ordinary skill in the art.

In one suitable embodiments, the present invention provides for immediate release carisoprodol formulations. Such formulations may comprise corisoprodol (for example, at a range of about 150-300 mg per tablet, and the excipients (amounts giver per tablet): about 5 to 80 mg corn starch, NF, powder; about 5 to 80 mg tribasic calcium phosphate, NF; about 2 to 25 mg alginic acid, NF; about 0.10 to 5 mg potassium sorbate, NF, powder and about 0.50 to 10 mg magnesium stearate, NF per mg of tablet.

Immediate release and extended release pharmaceutical composition can further comprise one or more additional active agents selected from the group consisting of non-aspirin NSAIDs, one or more muscle relaxing compounds, and one or more anxiolytic compounds, one or more narcotic analgesics, one or more non-narcotic analgesics, one or more anticonvulsants, one or more antipsychotics, and one or more antidepressants. In some embodiments, such a pharmaceutical composition provides for immediate release and extended release of carisoprodol for about 6 hours to about 24 hours.

In some embodiments of the present invention, the immediate release formulation can comprise from about 5% to about 20%, by weight of carisoprodol, or a pharmaceutically acceptable salt or ester thereof. In some embodiments, the pharmaceutical composition further comprises an one or more additional active agents in an amount of from about 0.1 to about 10 parts, from about 0.2 to about 8 parts, from about 0.3 to about 6 parts, from about 0.4 to about 5 parts, from about 0.5 to about 3 parts, or from about 0.5 to about 1 part of the carisoprodol by weight. The pharmaceutical composition can further comprise about 10% to about 90%, about 20% to about 80%, about 30% to about 70%, or about 40% to about 60% by weight of the hydrophilic carrier and the hydrodynamic diffusion enhancer, optionally with other pharmaceutically acceptable excipients or carriers.

In a suitable embodiment, the immediate release formulation may comprise (per tablet) about 100 to 300 mg of carisoprodol; about 5 to 100 mg of diclofenac potassium; about 5 to 80 mg of corn starch, NF, powder; about 5 to 80 mg of tribasic calcium phosphate, NF; about 2 to 25 mg of alginic acid, NF; about 0.10 to 5 mg potassium sorbate, powder; about 0.50 to 10 mg of magnesium stearate, NF (100 to 650 mg total).

In an additional embodiment of the invention, a formulation can comprise about 100 to 350 mg of carisoprodol; about 5 to 100 mg of diclofenac potassium; about 5 to 150 mg of ProSolv 90 HD; about 2 to 125 mg of Methocel E5 LV; about 2 to 80 mg of Sodium Starch Glycolate, NF; about 0.10 to 10 mg of colloidal silicon dioxide, NF; and about 0.50 to 10 mg of magnesium stearate, NF per mg of tablet (100 to 900 mg total).

Topical Formulations

In some embodiments, the present invention provides for the topical administration of carisoprodol, optionally with one or more additional active agents. For topical administration, the carisoprodol and optionally, the one or more one or more additional active agents, can be applied by any suitable topical therapeutic system, including, for example, creams, gels, liquids, aerosol or liquid sprays, and powders. For example, the carisoprodol and optionally, the one or more one or more additional active agents, can be formulated as a cream to be applied to the skin, resulting in the delivery of an effective amount or dose of carisoprodol and optionally, one or more additional active agents. The preparation and use of topical therapeutic systems are well known to those of skill in the art.

Transdermal Formulations

In some embodiments, the present invention provides for the transdermal administration of carisoprodol, optionally with one or more additional active agents. For transdermal administration, the carisoprodol and optionally, the one or more additional active agents, can be applied by any transdermal, therapeutic system that is consequently supplied to the organism, such as, for example, as a transdermal patch, transdermal cream or plaster. For example, the carisoprodol and optionally, the one or more additional active agents, can be formulated as a transdermal patch. The preparation and use of transdermal patches are well known to those of skill in the art and are available in different designs, including matrix-type or reservoir-type designs. In addition to the carisoprodol and optionally, the one or more additional active agents, transdermal patches can contain additional components such as penetration-enhancing agents and/or additional excipients that are conventionally employed, such as, e.g., carriers, gelling agents, suspending agents, dispersing agents, preservatives, stabilizers, wetting agents, emulsifying agents, and the like.

Dissolution Rates of the Pharmaceutical Formulations

U.S. Pat. Nos. 6,652,881 and 7,037,529 provide pharmaceutical compositions with distinct rates of dissolution of the active agents. In accordance with the above patents, the present invention provides controlled release pharmaceutical formulations suitable for oral administration, comprising carisoprodol or a pharmaceutically acceptable derivative, salt or ester thereof, and a pharmaceutically acceptable matrix adapted to provide a controlled release of carisoprodol or a pharmaceutically acceptable derivative, salt or ester thereof upon oral administration, having a dissolution rate in vitro when measured using (i) Apparatus 2 (paddle) described in USP 30 at 65 rpm in 1000 mL 0.1 N hydrochloric acid from 0 hours to 12 hours of dissolution, at 37.0±0.5° C. and using high performance liquid chromatography (HPLC) for quantification or (ii) Apparatus 1 (basket) described in USP 30 at 75 rpm in 1000 ml of 0.1 N hydrochloric acid containing 0.5% lauryl sulfate from 0 hours to 12 hours of dissolution at 37.0±0.5° C. and using high performance liquid chromatography (HPLC) for quantification:

Example of results obtained when using Apparatus 2 (paddle) at 65 rpm is provided below:

between 25 and 70% carisoprodol released in 30 minutes;
between 40 and 80% carisoprodol released in 1 hour;
between 60 and 90% carisoprodol released in 2 hours;
greater than 70% carisoprodol released in 4 hours;

greater than 85% carisoprodol released in 8 hours; and
greater than 95% carisoprodol released in 12 hours,
by weight of the label claim.

The present invention also provides for a method of treating or preventing musculoskeletal pain or muscle spasm or other non-malignant painful conditions in an animal suffering from or predisposed thereto, comprising orally administering to the animal a controlled release pharmaceutical formulation comprising carisoprodol or a pharmaceutically acceptable derivative, salt or ester thereof, and a pharmaceutically acceptable matrix adapted to provide a controlled release of carisoprodol or a pharmaceutically acceptable derivative, salt or ester thereof upon oral administration, having a dissolution rate in vitro when measured using (i) Apparatus 2 (paddle) described in USP 30 at 65 rpm in 1000 mL 0.1 N hydrochloric acid from 0 minutes to 12 hours of dissolution, at 37.0±0.5° C. and using high performance liquid chromatography (HPLC) for quantification or (ii) Apparatus 1 (basket) described in USP 30 at 75 rpm in 1000 ml of 0.1N hydrochloric acid containing 0.5% sodium lauryl sulfate from 0 hours to 12 hours of dissolution at 37.0±0.5° C. and using high performance liquid chromatography (HPLC) for quantification:

Example of results obtained when using Apparatus 2 (paddle) at 65 rpm is provided below:
between 25 and 70% carisoprodol released in 30 minutes;
between 40 and 80% carisoprodol released in 1 hour;
between 60 and 90% carisoprodol released in 2 hours;
greater than 70% carisoprodol released in 4 hours;
greater than 85% selodenoson released in 8 hours; and
greater than 95% carisoprodol released in 12 hours,
by weight of the label claim,
wherein the method results in a reduced level of sedation experienced by the animal compared to the level of sedation experienced by the animal upon administration of an immediate release composition comprising about 350 mg of carisoprodol, four times per day.

Methods of Use: Maintaining Effective Circulating Concentration of Active Compounds with Reduced Somnolence In additional embodiments, The present invention provides pharmaceutical compositions comprising an effective amount of carisoprodol with reduced somnolence. In some embodiments, the present invention provides a method of treating or preventing musculoskeletal pain or muscle spasm in an animal suffering from or predisposed thereto by administering to the animal a therapeutic amount of carisoprodol or a pharmaceutically acceptable derivative, salt or ester thereof, such that the administration results in the maintenance in the circulation of the animal of a therapeutic amount of carisoprodol or a pain- or spasm-treating or -preventing metabolite thereof from between 0.5 hours and 12 hours after administration of the carisoprodol or pharmaceutically acceptable derivative, salt or ester thereof and such that the musculoskeletal pain or muscle spasm is treated or prevented in the animal and the animal experiences a reduced level of sedation compared to the level of sedation experienced by the animal upon administration of an immediate release composition comprising about 350 mg of carisoprodol given four times per day. The method comprises administering to the animal a pharmaceutical composition containing about 250 mg of carisoprodol, or a pharmaceutically acceptable derivative, salt or ester thereof, and one or more pharmaceutically acceptable carriers or excipients, four times per day.

In some embodiments, the present invention provides a method of treating or preventing musculoskeletal pain or muscle spasm or other non-malignant painful conditions in an animal suffering from or predisposed thereto by administering to the animal a therapeutic amount of carisoprodol or a pharmaceutically acceptable derivative, salt or ester thereof, such that the administration results in the maintenance in the circulation of the animal of a therapeutic amount of carisoprodol or a pain- or spasm-treating or -preventing metabolite thereof from between 0.5 hours and 12 hours after administration of the carisoprodol or pharmaceutically acceptable derivative, salt or ester thereof and such that the musculoskeletal pain or muscle spasm is treated or prevented in the animal and the animal experiences a reduced level of sedation compared to the level of sedation experienced by the animal upon administration of a immediate release composition comprising about 350 mg of carisoprodol, four times per day.

In certain such embodiments, the method comprises orally administering to the animal one or more of the compositions of the invention as described herein, for example a controlled release pharmaceutical formulation comprising carisoprodol or a pharmaceutically acceptable derivative, salt or ester thereof, and a pharmaceutically acceptable matrix adapted to provide a controlled release of carisoprodol or a pharmaceutically acceptable derivative, salt or ester thereof upon oral administration, having a dissolution rate in vitro when measured using (i) Apparatus 2 (paddle) described in USP 30 at 65 rpm in 1000 mL 0.1 N hydrochloric acid from 0 minutes to 12 hours of dissolution, at 37.0±0.5° C. and using high performance liquid chromatography (HPLC) for quantification or (ii) Apparatus 1 (basket) described in USP 30 at 50 rpm in 1000 ml of 0.1N hydrochloric acid containing 0.5% sodium lauryl sulfate from 0 hours to 12 hours of dissolution at 37.0±0.5° C. and using high performance liquid chromatography (HPLC) for quantification.

Example of results obtained when using Apparatus 2 (paddle) at 65 rpm is provided below:
between 25 and 70% carisoprodol released in 30 minutes;
between 40 and 80% carisoprodol released in 1 hour;
between 60 and 90% carisoprodol released in 2 hours;
greater than 70% carisoprodol released in 4 hours;
greater than 85% carisoprodol released in 8 hours; and
greater than 95% carisoprodol released in 12 hours,
by weight of the label claim.

In certain such embodiments, the method comprises administering one or more of the compositions of the invention, for example a pharmaceutical composition comprising carisoprodol or a pharmaceutically acceptable derivative, salt or ester thereof, wherein the pharmaceutical composition produces somnolence or drowsiness in less than about 25%, less than about 20%, less than about 15%, or less than about 10% of animals to which it is administered, compared to placebo, as measured by spontaneous reporting of experiences during a randomized, double blind, placebo controlled study.

The present invention also provides methods and kits for treating or preventing musculoskeletal pain or muscle spasm or other non-malignant painful conditions by frequent dosing at a relatively low dosage of the active agent. In some embodiments, the present invention provides for a method of treating or preventing musculoskeletal pain or muscle spasm in an animal suffering from or predisposed thereto, comprising orally administering to the animal a pharmaceutical composition comprising about 25 mg to about 250 mg of carisoprodol, or a pharmaceutically acceptable derivative, salt or ester thereof, at least 3 times daily, wherein the method results in a reduced level of sedation experienced by the animal compared to the level of sedation experienced by the animal upon administration of an immediate release composition comprising about 350 mg of carisoprodol, at least 3 times daily. The pharmaceutical composition can further contain one or more additional active agents selected from the group consisting of non-aspirin NSAIDs, one or more muscle relaxing compounds, and one or more anxiolytic compounds, one or more narcotic analgesics, one or more non-narcotic analgesics, one or more anticonvulsants, one or more antipsychotics, and one or more antidepressants.

The present invention also provides a kit for treating or preventing musculoskeletal pain or muscle spasm or other non-malignant painful conditions in an animal suffering from or predisposed thereto, comprising at least 3 oral dosage forms for each day of treating or preventing musculoskeletal pain or muscle spasm in the animal, wherein each oral dosage form comprises about 25 mg to about 250 mg of carisoprodol, or a pharmaceutically acceptable derivative, salt or ester thereof, and a carrying component housing the oral dosage forms, wherein the carrying component indicates the time of day each dosage form should be administered to the animal. The carrying component can also be fitted with an alarm that will provide a signal when it is time to take the medication, thus serving as a reminder to facilitate compliance.

Clinical Indications

The compositions provided by the present invention are useful in methods for the treatment of a variety of physical disorders in animals (particularly mammals including humans) that are predisposed to or suffering from a physical disorder that may be delayed, prevented, cured or otherwise treated by the administration of carisoprodol or a pharmaceutically acceptable salt or ester thereof. Thus, in additional embodiments, the invention provides methods of treating or preventing such physical disorders, comprising administering an effective amount of one or more of the compositions of the invention to an animal (particularly a mammal, including a human) that is predisposed to or suffering from such a physical disorder. As used herein, an animal that is "predisposed to" a physical disorder is defined as an animal that does not exhibit a plurality of overt physical symptoms of the disorder but that is genetically, physiologically or otherwise at risk for developing the disorder. In such situations, the compositions of the present invention may thus be used prophylactically as chemopreventive agents for such disorders.

According to the invention, a mammal (preferably a human) that is predisposed to or suffering from a physical disorder may be treated by administering to the animal an effective dose of one or more of the pharmaceutical compositions of the present invention. Physical disorders treatable with the compositions and methods of the present invention include, but are not limited to, any physical disorder that is characterized by musculoskeletal pain or inflammation, muscle spasms (such as those associated with acute, painful musculoskeletal conditions), discomfort associated with musculoskeletal conditions, muscle pain, soreness, tightness, or tenderness, muscle strains or overexertion, injuries of the back and neck, and limitation of muscle movement. The compositions of the invention are also useful in treating or preventing the symptoms of such disorders, and thereby provide relief to patients suffering from or predisposed to such disorders Other non-malignant painful conditions may also be treatable with the compositions and methods of the present invention. Such non-malignant painful conditions include, but are not limited to, fibromyalgia, neuropathic pain, complex regional pain syndrome (previously known as reflex sympathetic dystrophy or RSD), painful conditions associated with central sensitization of various etiologies, spasticity associated with denervation injuries or degenerative neurological disease, hemifacial spasm, headache (for example, muscle tension type), exercise related pain (cramps, muscle soreness), delayed onset muscle pain, menstrual cramps, myalgia, and painful conditions associated with cerebral palsy or multiple sclerosis. The compositions and methods of the present invention can also be used to prevent the onset of non-malignant painful conditions such as exercise related pain (cramps, muscle soreness).

The pharmaceutical compositions of the present invention may be used as an adjunct to other measures (such as rest and physical therapy) for treating or preventing the symptoms of such disorders. The pharmaceutical compositions of the present invention which comprise carisoprodol and one or more additional active agents may also treat or prevent other disorders in addition to those referenced above. For example, in one embodiment of the present invention, the pharmaceutical composition comprises carisoprodol and the anxiolytic, diazepam (VALIUM®). Diazepam has a broad spectrum of indications (many that are off-label), including treatment of anxiety, panic attacks, state of agitation, epilepsy, alcohol and opiate withdrawal, insomnia, tetanus, mania, depression associated with anxiety, painful muscle conditions, spastic muscular paresis caused by cerebral or spinal cord conditions (such as stroke, multiple sclerosis, and spinal cord injury), drug-induced seizures, eclampsia, oxygen toxicity during hyperbaric oxygen therapy, irritable bowel syndrome, and pain resulting from muscle spasms caused by various spastic dystonias, including blepharospasm, spasmodic dysphonia, and Meige's Syndrome. A pharmaceutical composition of the present invention comprising carisoprodol and diazepam may have the same broad spectrum of indications as diazepam, in addition to its indication for the treatment or prevention of musculoskeletal conditions.

It will be readily apparent to one of ordinary skill in the relevant arts that other suitable modifications and adaptations to the methods and applications described herein may be made without departing from the scope of the invention or any embodiment thereof. It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the claims. Having now described the present invention in detail, the same will be more clearly understood by reference to the following examples, which are included herewith for purposes of illustration only and are not intended to be limiting of the invention.

EXAMPLES

Example 1

Comparison of the Induction of Somnolence by Carisoprodol and Meprobamate

Carisoprodol is a muscle relaxant analgesic, which has an active metabolite, meprobamate. Dalen et al. conducted an open three-panel single-dose administration study with 15 healthy volunteers: five poor metabolizers of mephenyloin, five poor metabolizers of debrisoquine and five extensive metabolizers of both substrates. The aim was to investigate if the elimination of carisoprodol and meprobamate is dependent on the two metabolic polymorphisms of mephenyloin and debrisoquine. The subjects were given single oral doses of 700 mg carisoprodol and 400 mg meprobamate on separate occasions. Dalen et al. concluded that the disposition of carisoprodol was clearly correlated to the mephenyloin hydroxylation phenotype. They concluded that mean serum clearance of carisoprodol was four times lower in poor metabolizers of mephenyloin than in extensive metabolizers, which they assert confirms the hypothesis from their previous study that N-dealkylation of carisoprodol cosegregates with the mephenyloin hydroxylation polymorphism. However, Dalen et al. indicated that mean serum clearance of meprobamate did not differ between the two groups. Also, polymorphic debrisoquine hydroxylation did not influence the elimination of carisoprodol or meprobamate. Dalen et al. further concluded that poor metabolizers of mephenyloin thus have a lower capacity to metabolize carisoprodol and may therefore have an increased risk of developing concentration dependent side-effects such as drowsiness and hypotension, if treated with ordinary doses of carisoprodol (see Dalen, P. et al, Pharmacogenetics. (1996) 6(5):387-94).

Figure 2:
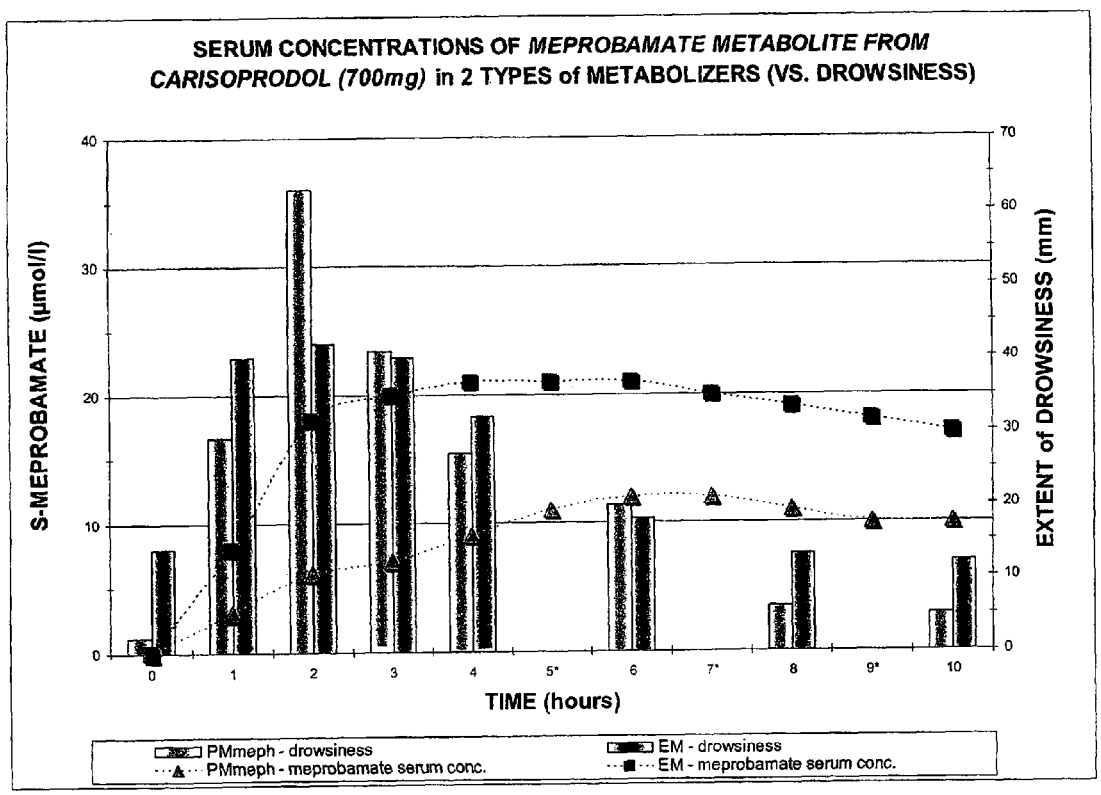
FIG. 2 shows a graph of the serum concentrations of meprobamate metabolite from carisoprodol (700 mg) in 2 types of metabolizers over time (versus drowsiness).
Figure 3:
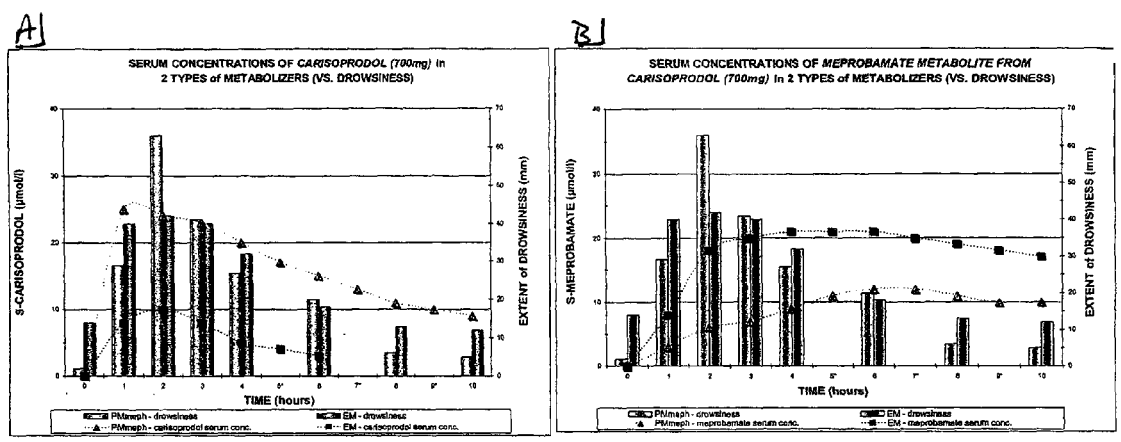
FIGS. 3A-3B show a side-by-side comparison of FIGS. 1 and 2.
Figure 4:
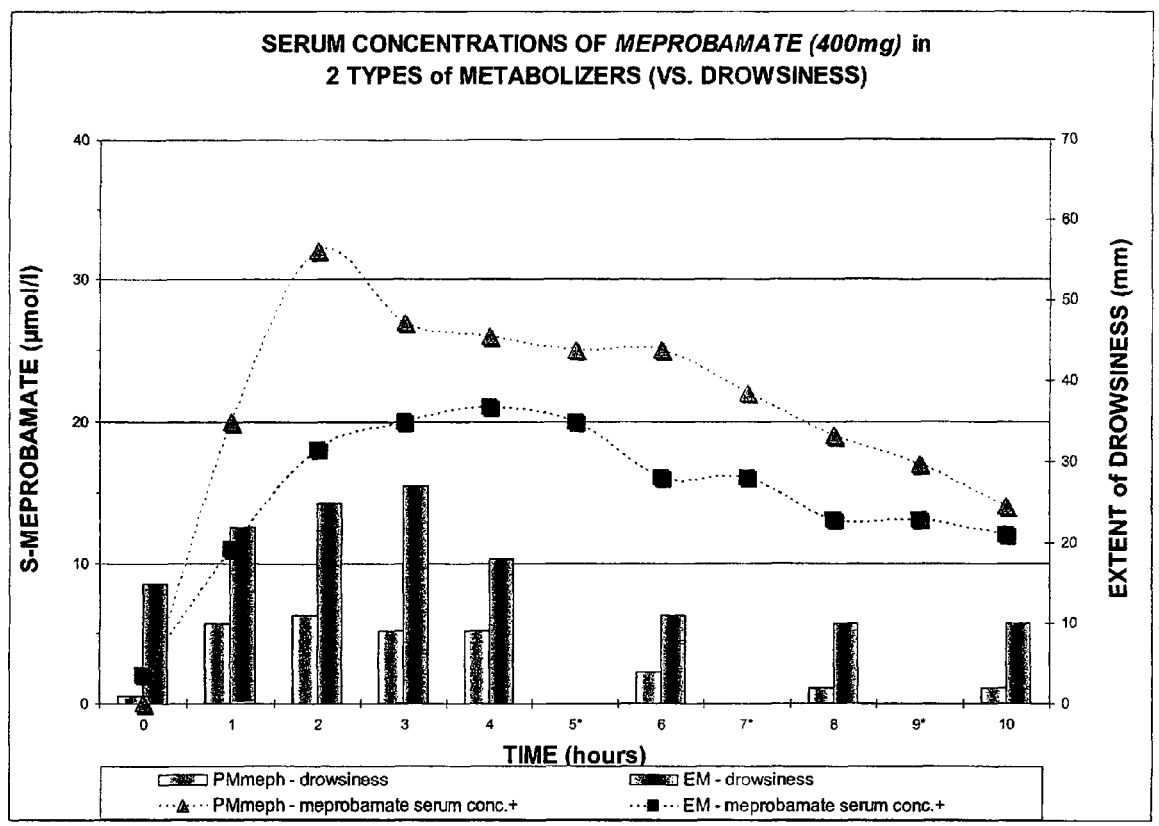
FIG. 4 shows a graph of the serum concentrations of meprobamate (400 mg) in 2 types of metabolizers over time (versus drowsiness).
Figure 5:
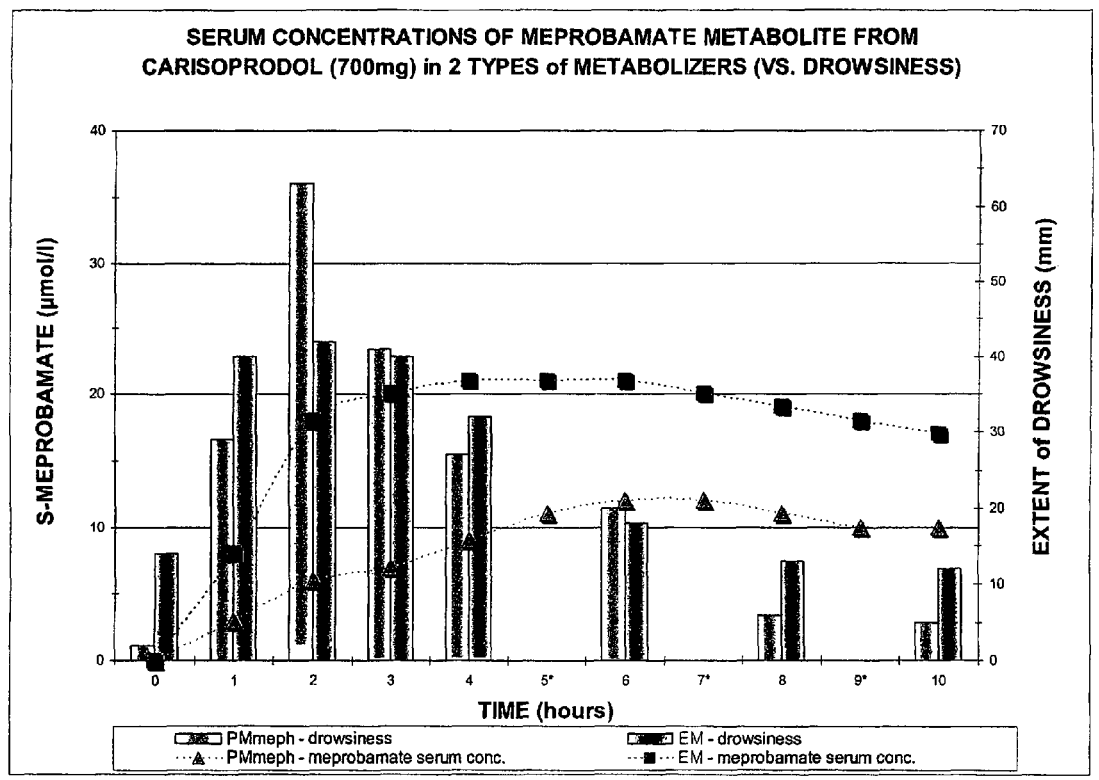
FIG. 5 shows a graph of the serum concentrations of meprobamate metabolite from carisoprodol (700 mg) in 2 types of metabolizers over time (versus drowsiness).
Figure 6:
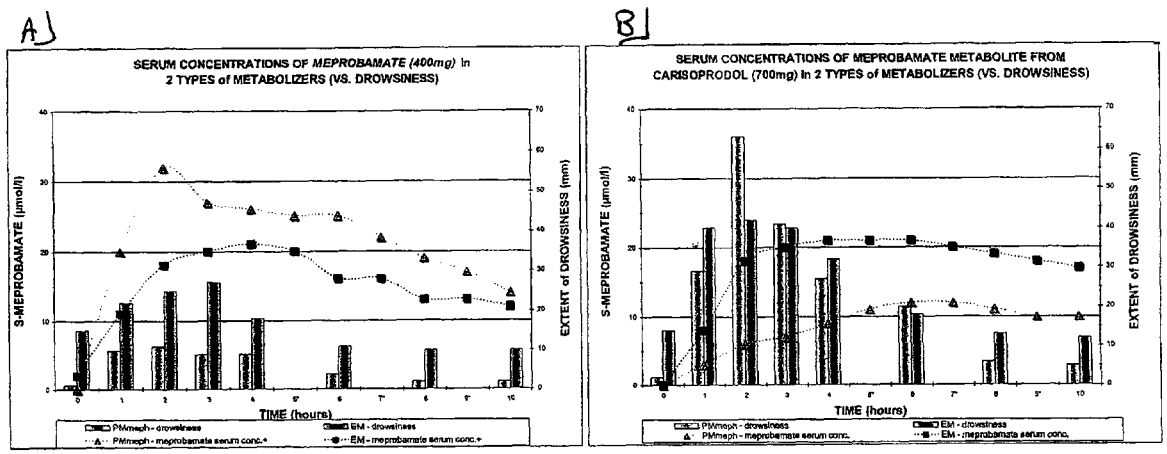
FIGS. 6A-6B show a side-by-side comparison of FIGS. 4 and 5.

FIGS. 1-6 show graphs of the serum concentrations of carisoprodol or meprobamate metabolite over time versus drowsiness. The role of meprobamate metabolite in effecting drowsiness is questionable from these graphs.

Example 2

Immediate Release Low Dose Carisoprodol Formulation

Table 1 shows an example of a carisoprodol immediate release formulation in accordance with the present invention.

TABLE 1

250 mg Carisoprodol Immediate Release Product

| Components | 250 mg strength |
|---|---|
| Carisoprodol, USP | 250.0 |
| Corn Starch, NF, Powder | 29.7 |
| Tribasic Calcium Phosphate, NF | 28.6 |
| Alginic Acid, NF | 7.14 |
| Potassium Sorbate, NF, Powder | 0.66 |
| Magnesium Stearate, NF | 2.9 |
| Total (mg) | 329 |

Example 3

Extended Release Carisoprodol Formulation

Tables 2a and 2b show examples of an extended release carisoprodol formulations in accordance with the present invention.

TABLE 2a

Carisoprodol Extended Release Product

| Components | % |
|---|---|
| Carisoprodol, USP (intragranular) | 58.5 |
| Carisoprodol, USP (extragranular) | 11.5 |
| ProSolv 90 HD | 5.75 |
| Methocel K100 Premium LV CR (Hypromellose 2208, USP) | 14 |
| Calcium Phosphate Dibasic, USP | QS |
| Sodium Starch Glycolate, NF | 4.0 |
| Colloidal Silicon Dioxide, NF | 0.5 |
| Magnesium Stearate, NF | 1.25 |
| Total Tablet Weight (mg/tab) | 100% |

TABLE 2b

Carisoprodol Extended Release Product

| Components | % |
|---|---|
| Carisoprodol, USP (intragranular) | 58.5 |
| Hypromellose E5 | 5 |
| Carisoprodol, USP (extragranular) | 11.5 |
| Methocel K100 Premium LV CR (Hypromellose 2208, USP) | 9 |
| ProSolv 90 HD | 5 |
| Calcium Phosphate Dibasic, USP | QS |
| Colloidal Silicon Dioxide, NF | 0.5 |
| Magnesium Stearate, NF | 1.25 |
| Total Tablet Weight (mg/tab) | 100% |

Example 4

Extended Release Carisoprodol/Diclofenac Combination Formulation

Table 3 shows an example of an extended release formulation comprising carisoprodol and diclofenac.

TABLE 3

700 mg Carisoprodol and 50 mg Diclofenac Extended Release Formulation.

| Intragranular Components | 700 mg strength |
|---|---|
| Carisoprodol, USP | 700.0 |
| Diclofenac potassium | 50 |
| ProSolv 90 HD | 57.5 |
| Methocel K100 Premium LV CR (Hypromellose 2208, USP) | 70.0 |
| Calcium Phosphate Dibasic, USP | 115.0 |
| Sodium Starch Glycolate, NF | 40.0 |
| Colloidal Silicon Dioxide, NF | 5.0 |
| Magnesium Stearate, NF | 12.5 |
| Total Tablet Weight (mg/tab) | 1000.0 |

Example 5

Low Dose Carisoprodol/Diclofenac Combination Formulation

Table 4 shows an example of a formulation comprising carisoprodol and diclofenac.

TABLE 4

250 mg Carisoprodol and 50 mg Diclofenac

| Intragranular Components | 250 mg strength |
|---|---|
| Carisoprodol, USP | 250 |
| Diclofenac potassium | 50 |
| ProSolv 90 HD | 43 |
| Methocel E5 LV | 20 |
| Sodium Starch Glycolate, NF | 32 |
| Colloidal Silicon Dioxide, NF | 2 |
| Magnesium Stearate, NF | 3 |
| Total (mg) | 400 |

Example 6

Immediate Release Carisoprodol/Diclofenac Combination Formulation

Table 5 shows an example of an immediate release formulation comprising carisoprodol and diclofenac.

TABLE 5

250 mg Carisoprodol and 50 mg Diclofenac Immediate Release Product

| Intragranular Components | 250 mg strength |
|---|---|
| Carisoprodol, USP | 250.0 |
| Diclofenac potassium | 50 |
| Corn Starch, NF, Powder | 29.7 |
| Tribasic Calcium Phosphate, NF | 28.6 |
| Alginic Acid, NF | 7.14 |
| Potassium Sorbate, NF, Powder | 0.66 |
| Magnesium Stearate, NF | 2.9 |
| Total (mg) | 329 |

Example 7

Carisoprodol 700 mg Sustained-Release Tablets

Components of Formulations 27-18a, 2718b, and 27-18c
Active Ingredient
Carisoprodol, USP
Inactive Ingredients
Hypromellose 2208, USP, 100 cps
Silicified Microcrystalline Cellulose (ProSolv HD® 90: silicified high-density microcrystalline cellulose composed of 98% microcrystalline cellulose, NF and 2% colloidal silicon dioxide, NF manufactured by JRS Pharma LP.)
Calcium Phosphate Dibasic, USP, Dihydrate Sodium Starch Glycolate, NF
Colloidal Silicon Dioxide, NF
Magnesium Stearate, NF
Components of Formulations 27-19a, 27-19b, and 27-19c
Active Ingredient
Carisoprodol, USP
Inactive Ingredients
Hypromellose 2910, USP, 5 cps
Hypromellose 2208, USP, 100 cps
Silicified Microcrystalline Cellulose
Calcium Phosphate Dibasic, USP, Dihydrate Colloidal Silicon Dioxide, NF
Magnesium Stearate, NF
Quantitative Composition
Quantitative Composition for Formulation 27-18a

| Ingredient | % w/w | mg/Tablet | Quantity (kg) for 95,000 Tablets |
|---|---|---|---|
| Carisoprodol, USP | 70.00 | 700.00 | 66.50 |
| Hypromellose 2208, USP, 100 cps | 7.00 | 70.00 | 6.65 |
| Silicified Microcrystalline Cellulose | 5.75 | 57.50 | 5.46 |
| Calcium Phosphate Dibasic, USP, Dihydrate | 11.50 | 115.00 | 10.93 |
| Sodium Starch Glycolate, NF | 4.00 | 40.00 | 3.80 |
| Colloidal Silicon Dioxide, NF | 0.50 | 5.00 | 0.48 |
| Magnesium Stearate, NF | 1.25 | 12.50 | 1.19 |
| Total | 100.00 | 1000.00 | 95.01 |

Quantitative Composition for Formulation 27-18b

| Ingredient | % w/w | mg/Tablet | Quantity (kg) for 95,000 Tablets |
|---|---|---|---|
| Carisoprodol, USP | 70.00 | 700.00 | 66.50 |
| Hypromellose 2208, USP, 100 cps | 14.00 | 140.00 | 13.30 |
| Silicified Microcrystalline Cellulose | 5.75 | 57.50 | 5.46 |
| Calcium Phosphate Dibasic, USP, Dihydrate | 4.50 | 45.00 | 4.28 |
| Sodium Starch Glycolate, NF | 4.00 | 40.00 | 3.80 |
| Colloidal Silicon Dioxide, NF | 0.50 | 5.00 | 0.48 |
| Magnesium Stearate, NF | 1.25 | 12.50 | 1.19 |
| Total | 100.00 | 1000.00 | 95.01 |

Quantitative Composition for Formulation 27-18c

| Ingredient | % w/w | mg/Tablet | Quantity (kg) for 95,000 Tablets |
|---|---|---|---|
| Carisoprodol, USP | 70.00 | 700.00 | 66.50 |
| Hypromellose 2208, USP, 100 cps | 18.00 | 180.00 | 17.10 |
| Silicified Microcrystalline Cellulose | 5.75 | 57.50 | 5.46 |
| Calcium Phosphate Dibasic, USP, Dihydrate | 0.50 | 5.00 | 0.48 |
| Sodium Starch Glycolate, NF | 4.00 | 40.00 | 3.80 |
| Colloidal Silicon Dioxide, NF | 0.50 | 5.00 | 0.48 |
| Magnesium Stearate, NF | 1.25 | 12.50 | 1.19 |
| Total | 100.00 | 1000.00 | 95.01 |

Quantitative Composition for Formulation 27-19a

| Ingredient | % w/w | mg/Tablet | Quantity (kg) for 95,000 Tablets |
|---|---|---|---|
| Carisoprodol, USP | 70.00 | 700.00 | 66.50 |
| Hypromellose 2910, USP, 5 cps | 5.00 | 50.00 | 4.75 |
| Hypromellose 2208, USP, 100 cps | 5.00 | 50.00 | 4.75 |
| Silicified Microcrystalline Cellulose | 5.00 | 50.00 | 4.75 |
| Calcium Phosphate Dibasic, USP, Dihydrate | 13.25 | 132.50 | 12.59 |
| Colloidal Silicon Dioxide, NF | 0.50 | 5.00 | 0.48 |
| Magnesium Stearate, NF | 1.25 | 12.50 | 1.19 |
| Total | 100.00 | 1000.00 | 95.01 |

Quantitative Composition for Formulation 27-19b

| Ingredient | % w/w | mg/Tablet | Quantity (kg) for 95,000 Tablets |
|---|---|---|---|
| Carisoprodol, USP | 70.00 | 700.00 | 66.50 |
| Hypromellose 2910, USP, 5 cps | 5.00 | 50.00 | 4.75 |
| Hypromellose 2208, USP, 100 cps | 9.00 | 90.00 | 8.55 |
| Silicified Microcrystalline Cellulose | 5.00 | 50.00 | 4.75 |
| Calcium Phosphate Dibasic, USP, Dihydrate | 9.25 | 92.50 | 8.79 |
| Colloidal Silicon Dioxide, NF | 0.50 | 5.00 | 0.48 |
| Magnesium Stearate, NF | 1.25 | 12.50 | 1.19 |
| Total | 100.00 | 1000.00 | 95.01 |

Quantitative Composition for Formulation 27-19c

| Ingredient | % w/w | mg/Tablet | Quantity (kg) for 95,000 Tablets |
|---|---|---|---|
| Carisoprodol, USP | 70.00 | 700.00 | 66.50 |
| Hypromellose 2910, USP, 5 cps | 5.00 | 50.00 | 4.75 |
| Hypromellose 2208, USP, 100 cps | 11.00 | 110.00 | 10.45 |
| Silicified Microcrystalline Cellulose | 5.00 | 50.00 | 4.75 |
| Calcium Phosphate Dibasic, USP, Dihydrate | 7.25 | 72.50 | 6.89 |
| Colloidal Silicon Dioxide, NF | 0.50 | 5.00 | 0.48 |
| Magnesium Stearate, NF | 1.25 | 12.50 | 1.19 |
| Total | 100.00 | 1000.00 | 95.01 |

Ingredient Functional Category

| Ingredient | Functional Category |
|---|---|
| Carisoprodol, USP | Active |
| Hypromellose 2910, USP, 5 cps | Binder, Release Controlling Agent |
| Hypromellose 2208, USP, 100 cps | Release Controlling Agent |
| Silicified Microcrystalline Cellulose | Diluent |
| Calcium Phosphate Dibasic, USP | Diluent |
| Sodium Starch Glycolate, NF | Disintegrant |
| Colloidal Silicon Dioxide, NF | Glidant |
| Magnesium Stearate, NF | Lubricant |

Manufacturing Directions for Formulations 27-18a, 27-18b, and 27-18c

Granulation

A portion of the Carisoprodol, USP and Hypromellose 2208, USP, 100 cps are mixed in a Zanchetta high intensity mixer and wet granulated using Purified Water, USP.

The wet granulation is spread onto trays and dried in an oven to an LOD of <2.0%.

The dried granulation is milled using a Fitzmill and #2 screen.

Blending

Carisoprodol, USP (remaining portion), Silicified Microcrystalline Cellulose, Calcium Phosphate Dibasic, USP, Dihydrate, Sodium Starch Glycolate, NF, and Colloidal Silicon Dioxide, NF are passed through a #14 stainless steel mesh screen.

The milled granulation from above is mixed in a 10 cu. ft. twin-shell blender with the screened material for 15 minutes.

Magnesium Stearate, NF is passed through a #20 stainless steel mesh screen, added to the blend in the 10 cu. ft. twin-shell blender, and mixed for 4 minutes. The final blend is discharged into polyethylene-lined containers.

Tablet Compression

The granulation is compressed into tablets using a rotary tablet press to achieve a target weight of 1000 mg/tablet.

Manufacturing Directions for Formulations 27-19a, 27-19b, and 27-19c

Granulation

A portion of the Carisoprodol, USP and Hypromellose 2910, USP, 5 cps are mixed in a Zanchetta high intensity mixer and wet granulated using Purified Water, USP.

The wet granulation is spread onto trays and dried in an oven to an LOD of <2.0%.

The dried granulation is milled using a Fitzmill and #2 screen.

Blending

Carisoprodol, USP (remaining portion), Hypromellose 2208, USP, 100 cps, Silicified Microcrystalline Cellulose, Calcium Phosphate Dibasic, USP, Dihydrate, and Colloidal Silicon Dioxide, NF are passed through a #14 stainless steel mesh screen.

The milled granulation from above is mixed in a 10 cu. ft. twin-shell blender with the screened material for 15 minutes.

Magnesium Stearate, NF is passed through a #20 stainless steel mesh screen, added to the blend in the 10 cu. ft. twin-shell blender, and mixed for 4 minutes. The final blend is discharged into polyethylene-lined containers.

Tablet Compression

The granulation is compressed into tablets using a rotary tablet press to achieve a target weight of 1000 mg/tablet.

In-Process Limits:

Tablet Weight (n=10): Target: 10.00 g (Range: 9.70-10.30 g)

Average Hardness (n=10): Target: 20 SCU (Range: 15-25 SCU)

Average Thickness (n=10): Target: 6.75 mm (Range: 6.25-7.25 mm)

Friability (n=10): Target: 1% maximum

The present invention has been described with reference to certain embodiments thereof. However, the scope of the invention is not limited to the embodiments described or exemplified. Workers of ordinary skill in the relevant arts will readily appreciate that other embodiments and examples can be practiced without departing from the scope of the present invention. All such variations are considered to be part of, and therefore encompassed by, the present invention.

All publications, patents and patent applications mentioned or referenced in this specification are herein incorporated by reference to the same extent as if each individual publication, patent or patent application was specifically and individually indicated to be incorporated by reference.

What is claimed is:

1. A controlled release pharmaceutical formulation suitable for oral administration, comprising carisoprodol or a pharmaceutically acceptable, salt or ester thereof, and a pharmaceutically acceptable matrix adapted to provide a controlled release of carisoprodol or a pharmaceutically acceptable, salt or ester thereof upon oral administration, said controlled release pharmaceutical formulation having a dissolution rate in vitro when measured using Apparatus 2 (paddle) described in USP 30 at 65 rpm in 1000 ml of 0.1N hydrochloric acid from 0 hours to 12 hours of dissolution at 37.0±0.5° C. and using high performance liquid chromatography (HPLC) for quantification:

between 25 and 70% carisoprodol released in 30 minutes;
between 40 and 80% carisoprodol released in 1 hour;
between 60 and 90% carisoprodol released in 2 hours;
greater than 70% carisoprodol released in 4 hours;
greater than 85% carisoprodol released in 8 hours; and
greater than 95% carisoprodol released in 12 hours,
by weight of the label claim, wherein said carisoprodol or a pharmaceutically acceptable derivative, salt or ester thereof has a particle size such that either (a) about 100% of the particles have an average size of less than about 50 microns; or (b) greater than about 40% of the particles are about 250 microns or greater.

2. The controlled release pharmaceutical formulation of claim 1, wherein said controlled release pharmaceutical formulation further comprises one or more additional active agents selected from the group consisting of at least one non-aspirin NSAID, one or more muscle relaxing compounds, one or more anxiolytic compounds, one or more narcotic analgesics, one or more non-narcotic analgesics, one or more anticonvulsants, one or more antipsychotics, and one or more antidepressants.

3. The controlled release pharmaceutical formulation of claim 2, wherein said one or more additional active agents is at least one non-aspirin NSAID.

4. The controlled release pharmaceutical formulation of claim 3, wherein said non-aspirin NSAID is selected from the group consisting of ketorolac, aceclofenac, ibuprofen and naproxen, and pharmaceutically acceptable, salts or esters thereof.

5. The controlled release pharmaceutical formulation of claim 1 or claim 2, wherein said formulation is in the form of a capsule filled with a plurality of controlled release pellets coated with a controlled release film coat.

6. The controlled release pharmaceutical formulation of claim 1 or claim 2, wherein said formulation is in the form of a hydrophilic or hydrophobic tablet.

7. The controlled release pharmaceutical formulation of claim 1 or claim 2, wherein said formulation is suitable for dosing every 12 or more hours.

8. The controlled release pharmaceutical formulation of claim 1, wherein said controlled release pharmaceutical formulation comprises about 400 mg to about 1000 mg of carisoprodol or a pharmaceutically acceptable, salt or ester thereof.

9. The controlled release pharmaceutical formulation of claim 8, wherein said formulation comprises about 700 mg of carisoprodol or a pharmaceutically acceptable, salt or ester thereof.

10. The controlled release pharmaceutical formulation claim 1 or claim 2, wherein said controlled release pharmaceutical formulation is in the form of a tablet, a capsule, a sachet, or a plurality of multiparticulates.

11. The controlled release pharmaceutical formulation of claim 10, wherein said plurality of multiparticulates comprises a plurality of granules, spheroids or pellets.

12. A method of treating musculoskeletal pain or muscle spasm or other non-malignant painful conditions in an animal suffering from or predisposed thereto, said method comprising orally administering an effective amount of the controlled release pharmaceutical formulation of claim 1 or claim 2 to the animal.

13. The method of claim 12, wherein said pharmaceutically acceptable matrix is adapted to provide said controlled release having said dissolution rate in vitro,
wherein said method results in a reduced level of sedation experienced by said animal compared to the level of sedation experienced by said animal upon administration of an immediate release composition comprising about 350 mg of carisoprodol administered four times daily.

14. The method of claim 13, wherein said controlled release pharmaceutical formulation further comprises one or more additional active agents selected from the group consisting of at least one non-aspirin NSAID, one or more muscle relaxing compounds, one or more anxiolytic compounds, one or more narcotic analgesics, one or more non-narcotic analgesics, one or more anticonvulsants, one or more antipsychotics, and one or more antidepressants.

15. The method of claim 14, wherein said one or more additional active agents is at least one non-aspirin NSAID.

16. The method of claim 15, wherein said non-aspirin NSAID is selected from the group consisting of ketorolac, aceclofenac, ibuprofen and naproxen, and pharmaceutically acceptable, salts or esters thereof.

17. The method of claim 12, wherein said orally administering an effective amount of said controlled release pharmaceutical formulation results in the maintenance in the circulation of said animal of an amount of carisoprodol or a metabolite thereof that is sufficient to treat pain or spasm from between 0.5 hours and 12 hours after administration of said carisoprodol or pharmaceutically acceptable, salt or ester thereof.

18. The method of claim 17, wherein said controlled release pharmaceutical formulation further comprises one or more additional active agents selected from the group consisting of at least one non-aspirin NSAID, one or more muscle relaxing compounds, one or more anxiolytic compounds, one or more narcotic analgesics, one or more non-narcotic analgesics, one or more anticonvulsants, one or more antipsychotics, and one or more antidepressants.

19. The method of claim 18, wherein said one or more additional active agents is at least one non-aspirin NSAID.

20. The method of claim 19, wherein said non-aspirin NSAID is selected from the group consisting of ketorolac, aceclofenac, ibuprofen and naproxen, and pharmaceutically acceptable, salts or esters thereof.

21. A pharmaceutical composition comprising carisoprodol, or a pharmaceutically acceptable, salt or ester thereof, and one or more additional active agents selected from the group consisting of non-aspirin NSAID, one or more muscle relaxing compounds, one or more anxiolytic compounds, one or more narcotic analgesics, one or more non-narcotic analgesics, one or more anticonvulsants, one or more antipsychotics, and one or more antidepressants, said composition having a dissolution rate in vitro when measured using Apparatus 2 (paddle) described in USP 30 at 65 rpm in 1000 ml of 0.1N hydrochloric acid from 0 hours to 12 hours of dissolution at $37.0 \pm 0.5°$ C. and using high performance liquid chromatography (HPLC) for quantification:
between 25 and 70% carisoprodol released in 30 minutes;
between 40 and 80% carisoprodol released in 1 hour;
between 60 and 90% carisoprodol released in 2 hours;
greater than 70% carisoprodol released in 4 hours;
greater than 85% carisoprodol released in 8 hours; and
greater than 95% carisoprodol released in 12 hours,
by weight of the label claim
wherein said pharmaceutical composition provides for extended release of said carisoprodol or both said carisoprodol and said one or more additional active agents from said pharmaceutical composition for a period of about 6 hours to about 24 hours,
wherein said carisoprodol or a pharmaceutically acceptable, salt or ester thereof has a particle size such that either (a) about 100% of the particles have an average size of less than about 50 microns, or (b) greater than about 40% of the particles are about 250 microns or greater.

22. The pharmaceutical composition of claim 21, wherein said composition provides for extended release of carisoprodol, pharmaceutically acceptable, salt or ester thereof, without providing for extended release of said one or more additional active agents.

23. The pharmaceutical composition of claim 21, wherein said composition provides for extended release of said carisoprodol, or pharmaceutically acceptable, salt or ester thereof, and said one or more additional active agents.

24. The pharmaceutical composition of claim 21, wherein said composition comprises about 500 mg to about 900 mg of carisoprodol, or a pharmaceutically acceptable, salt or ester thereof.

25. The pharmaceutical composition of claim 21, wherein said composition comprises about 700 mg of carisoprodol, or a pharmaceutically acceptable, salt or ester thereof.

26. The pharmaceutical composition of claim 21, wherein said non-aspirin NSAID is selected from the group consisting of ketorolac, aceclofenac, ibuprofen and naproxen, and pharmaceutically acceptable, salts or esters thereof.

27. The pharmaceutical composition of claim 21, wherein said composition is formulated for oral administration.

28. The pharmaceutical composition of claim 21, wherein said composition is formulated for topical or parenteral administration.

29. The pharmaceutical composition of claim 21, wherein said composition is in the form of a tablet comprising:
  (i) said carisoprodol, pharmaceutically acceptable, salt or ester thereof, or both of said carisoprodol, pharmaceutically acceptable, salt or ester thereof and said one or more additional active agents; and
  (ii) at least one functional coating surrounding said carisoprodol, pharmaceutically acceptable, salt or ester thereof which provides for extended release of said carisoprodol, pharmaceutically acceptable, salt or ester thereof or both of said carisoprodol, pharmaceutically acceptable, salt or ester thereof and said active agent for a period of greater than about 12 hours.

30. The pharmaceutical composition of claim 21, wherein said composition is in the form of a tablet and wherein said carisoprodol, pharmaceutically acceptable, salt or ester thereof or both of said carisoprodol, pharmaceutically acceptable, salt or ester thereof and said one or more additional active agents is bound to at least one ion exchanger and provides extended release of said carisoprodol or both said carisoprodol and said active agent for a period of greater than about 12 hours.

31. The pharmaceutical composition of claim 21, wherein said composition is in the form of a tablet, and wherein said carisoprodol, pharmaceutically acceptable, salt or ester thereof or both of said carisoprodol, pharmaceutically acceptable, salt or ester thereof and said one or more additional active agents are embedded in an embedding substance and provides extended release of said carisoprodol, pharmaceutically acceptable, salt or ester thereof or both of said carisoprodol, pharmaceutically acceptable, salt or ester thereof and said active agent for a period of greater than about 12 hours.

32. A method of treating musculoskeletal pain or muscle spasm or other non-malignant painful conditions in an animal suffering from or predisposed thereto, said method comprising administering an effective amount of the controlled release pharmaceutical composition of claim 21 to the animal.

33. A pharmaceutical composition for controlled onset and extended release of carisoprodol, said composition comprising:
  (a) a core comprising:
    (i) carisoprodol or a pharmaceutically acceptable, salt or ester thereof;
    (ii) a hydrophilic carrier;
    (iii) a hydrodynamic diffusion enhancer; and optionally
    (iv) conventional pharmaceutically acceptable excipients selected from the group consisting of binders, fillers and lubricants and combinations thereof; and
  (b) a functional coating membrane surrounding said core, and optionally
  (c) a seal coating membrane between the core and the functional coating membrane, and optionally
  (d) a top coating membrane surrounding the functional coating membrane;
  wherein said composition comprises a nanoparticle-based delivery system with embedded carisoprodol or a pharmaceutically acceptable, salt or ester thereof,
  wherein said composition provides an extended release of the carisoprodol, pharmaceutically acceptable, salt or ester thereof from the composition for about 12 to about 24 hours wherein said carisoprodol or a pharmaceutically acceptable salt or ester thereof has a particle size such that either (a) about 100% of the particles have an average size of less than about 50 microns, or (b) greater than about 40% of the particles are about 250 microns or greater,
  said composition having a dissolution rate in vitro when measured using Apparatus 2 (paddle) described in USP 30 at 65 rpm in 1000 ml of 0.1N hydrochloric acid from 0 hours to 12 hours of dissolution at 37.0±0.5° C. and using high performance liquid chromatography (HPLC) for quantification:
    between 25 and 70% carisoprodol released in 30 minutes:
    between 40 and 80% carisoprodol released in 1 hour;
    between 60 and 90% carisoprodol released in 2 hours;
    greater than 70% carisoprodol released in 4 hours;
    greater than 85% carisoprodol released in 8 hours; and
    greater than 95% carisoprodol released in 12 hours,
    by weight of the label claim.

34. The pharmaceutical composition of claim 33, further comprising one or more additional active agents selected from the group consisting of non-aspirin NSAIDs, one or more muscle relaxing compounds, and one or more anxiolytic compounds, one or more narcotic analgesics, one or more non-narcotic analgesics, one or more anticonvulsants, one or more antipsychotics, and one or more antidepressants.

35. The pharmaceutical composition of claim 33, wherein said pharmaceutical composition provides for controlled onset and extended release of said one or more additional active agents for a period greater than 12 hours.

36. A pharmaceutical composition comprising carisoprodol, or a pharmaceutically acceptable, salt or ester thereof wherein said carisoprodol or a pharmaceutically acceptable salt or ester thereof has a particle size such that either (a) about 100% of the particles have an average size of less than about 50 microns, or (b) greater than about 40% of the particles are about 250 microns or greater said composition having a dissolution rate in vitro when measured using Apparatus 2 (paddle) described in USP 30 at 65 rpm in 1000 ml of 0.1N hydrochloric acid from 0 hours to 12 hours of dissolution at 37.0±0.5° C. and using high performance liquid chromatography (HPLC) for quantification:
    between 25 and 70% carisoprodol released in 30 minutes;
    between 40 and 80% carisoprodol released in 1 hour;
    between 60 and 90% carisoprodol released in 2 hours;
    greater than 70% carisoprodol released in 4 hours;
    greater than 85% carisoprodol released in 8 hours; and
    greater than 95% carisoprodol released in 12 hours,
    by weight of the label claim, wherein said pharmaceutical composition produces somnolence or drowsiness in less than about 15% of animals to which it is administered, compared to placebo, as measured by spontaneous reporting of experiences during a randomized, double blind, placebo controlled study.

37. The pharmaceutical composition of claim 36, further comprising one or more additional active agents selected from the group consisting of non-aspirin NSAIDs, one or more muscle relaxing compounds, one or more anxiolytic compounds, one or more narcotic analgesics, one or more non-narcotic analgesics, one or more anticonvulsants, one or more antipsychotics, and one or more antidepressants.

38. A pharmaceutical composition comprising:
  (a) about 700 mg of carisoprodol, or a pharmaceutically acceptable, salt or ester thereof;

(b) about 50 mg to about 140 mg of hypromellose 2208, USP, 100 cps;
(c) optionally, about 50 mg of hypromellose 2910, USP, 5 cps;
(d) about 50 mg to about 57.5 mg of silicified microcrystalline cellulose;
(e) about 5 mg to about 132.5 mg of calcium phosphate dibasic, USP, dihydrate;
(f) optionally, about 40 mg of sodium starch glycolate, NF;
(g) about 5 mg of colloidal silicon dioxide, NF; and
(h) about 12.5 mg of magnesium stearate,
wherein said carisoprodol or a pharmaceutically acceptable, salt or ester thereof has a particle size such that either (a) about 100% of the particles have an average size of less than about 50 microns, or (b) greater than about 40% of the particles are about 250 microns or greater.

39. The pharmaceutical composition of claim 38, wherein said composition consists essentially of about 700 mg of carisoprodol, or a pharmaceutically acceptable, salt or ester thereof.

40. The pharmaceutical composition of claim 38, wherein said composition further comprises one or more additional active agents selected from the group consisting of at least one non-aspirin NSAID, one or more muscle relaxing compounds, one or more anxiolytic compounds, one or more narcotic analgesics, one or more non-narcotic analgesics, one or more anticonvulsants, one or more antipsychotics, and one or more antidepressants.

41. The pharmaceutical composition of claim 40, wherein said one or more additional active agents is one or more non-aspirin NSAID.

42. The pharmaceutical composition of claim 41, wherein said non-aspirin NSAID is selected from the group consisting of ketorolac, aceclofenac, acetaminophen, ibuprofen and naproxen, and pharmaceutically acceptable, salts and esters thereof.

43. The pharmaceutical composition of claim 38 or claim 40, wherein said composition is formulated for oral administration.

44. The pharmaceutical composition of claim 38 or claim 40, wherein said composition is formulated for topical or parenteral administration.

45. A method of treating or preventing musculoskeletal pain or muscle spasm or other non-malignant painful conditions in an animal suffering from or predisposed thereto, comprising administering an effective amount of the pharmaceutical composition of claim 38 or claim 40 to the animal.

* * * * *

UNITED STATES PATENT AND TRADEMARK OFFICE
CERTIFICATE OF CORRECTION

PATENT NO. : 8,895,061 B2
APPLICATION NO. : 12/529674
DATED : November 25, 2014
INVENTOR(S) : Balwani et al.

It is certified that error appears in the above-identified patent and that said Letters Patent is hereby corrected as shown below:

In the claims,

In claim 1, column 44, line 37, replace "acceptable," with --acceptable--.

In claim 1, column 44, lines 39-40, replace "acceptable," with --acceptable--.

In claim 1, column 44, line 42, replace "in vitro" with --*in vitro*--.

In claim 1, column 44, lines 54-55, replace "acceptable derivative, salt" with --acceptable salt--.

In claim 4, column 45, line 9, replace "acceptable," with --acceptable--.

In claim 8, column 45, line 24, replace "acceptable," with --acceptable--.

In claim 9, column 45, line 28, replace "acceptable," with --acceptable--.

In claim 13, column 45, line 45, replace "in vitro" with --*in vitro*--.

In claim 16, column 45, line 65, replace "acceptable," with --acceptable--.

In claim 17, column 46, line 5, replace "acceptable," with --acceptable--.

In claim 20, column 46, line 20, replace "acceptable," with --acceptable--.

In claim 21, column 46, line 22, replace "acceptable," with --acceptable--.

In claim 21, column 46, lines 46-47, replace "acceptable," with --acceptable--.

In claim 21, column 46, line 29, replace "in vitro" with --*in vitro*--.

In claim 21, column 46, line 40, replace "label claim" with --label claim,--.

In claim 22, column 46, line 54, replace "acceptable," with --acceptable--.

Signed and Sealed this
Twenty-first Day of July, 2015

Michelle K. Lee
*Director of the United States Patent and Trademark Office*

CERTIFICATE OF CORRECTION (continued)
U.S. Pat. No. 8,895,061 B2

In claim 23, column 46, line 59, replace "acceptable," with --acceptable--.

In claim 24, column 46, line 63, replace "acceptable," with --acceptable--.

In claim 25, column 46, line 67, replace "acceptable," with --acceptable--.

In claim 26, column 47, line 4, replace "acceptable," with --acceptable--.

In claim 29, column 47, line 12, replace "acceptable," with --acceptable--.

In claim 29, column 47, line 14, replace "acceptable," with --acceptable--.

In claim 29, column 47, line 17, replace "acceptable," with --acceptable--.

In claim 29, column 47, line 19, replace "acceptable," with --acceptable--.

In claim 29, column 47, line 21, replace "acceptable," with --acceptable--.

In claim 30, column 47, line 25, replace "acceptable," with --acceptable--.

In claim 30, column 47, lines 26-27, replace "acceptable," with --acceptable--.

In claim 31, column 47, line 34, replace "acceptable," with --acceptable--.

In claim 31, column 47, lines 35-36, replace "acceptable," with --acceptable--.

In claim 31, column 47, line 39, replace "acceptable," with --acceptable--.

In claim 31, column 47, line 40, replace "acceptable," with --acceptable--.

In claim 33, column 47, line 52, replace "acceptable," with --acceptable--.

In claim 33, column 47, line 67, replace "acceptable," with --acceptable--.

In claim 33, column 48, line 2, replace "acceptable," with --acceptable--.

In claim 33, column 48, line 4, replace "24 hours" with --24 hours,--.

In claim 33, column 48, line 10, replace "in vitro" with --*in vitro*--.

In claim 36, column 48, line 35, replace "acceptable," with --acceptable--.

In claim 36, column 48, line 35, replace "ester thereof" with --ester thereof,--.

In claim 36, column 48, line 40, replace "or greater" with --or greater,--.

In claim 36, column 48, line 41, replace "in vitro" with --*in vitro*--.

In claim 38, column 48, line 67, replace "acceptable," with --acceptable--.

In claim 38, column 49, lines 12-13, replace "acceptable," with --acceptable--.

CERTIFICATE OF CORRECTION (continued)
U.S. Pat. No. 8,895,061 B2

In claim 39, column 49, line 20, replace "acceptable," with --acceptable--.

In claim 42, column 50, line 11, replace "acceptable," with --acceptable--.

In claim 45, column 50, line 20, replace "treating or preventing musculoskeletal" with --treating musculoskeletal--.